US012778656B2

(12) United States Patent
Hartman et al.

(10) Patent No.: US 12,778,656 B2
(45) Date of Patent: Nov. 3, 2026

(54) VESSEL MODIFICATION USING COLD THERAPY

(71) Applicant: Medtronic Vascular, Inc., Santa Rosa, CA (US)

(72) Inventors: Christopher P. Hartman, Rohnert Park, CA (US); Stefan S. Tunev, Santa Rosa, CA (US); Carlos H. Lima, Santa Rosa, CA (US); Richard J. Bliss, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 951 days.

(21) Appl. No.: 18/051,272

(22) Filed: Oct. 31, 2022

(65) Prior Publication Data

US 2023/0165618 A1 Jun. 1, 2023

Related U.S. Application Data

(60) Provisional application No. 63/284,358, filed on Nov. 30, 2021.

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00577* (2013.01); *A61B 2018/0212* (2013.01)

(58) Field of Classification Search
CPC ............ A61B 18/02; A61B 2018/0022; A61B 2018/00577; A61B 2018/0212; A61F 7/12; A61F 7/123; A61F 2007/126
See application file for complete search history.

(56) References Cited

U.S. PATENT DOCUMENTS 6,080,171 A 6/2000 Keith et al.
6,241,718 B1 6/2001 Arless et al.
(Continued)

FOREIGN PATENT DOCUMENTS

EP 1894534 A2 3/2008
EP 2763624 B1 11/2020
(Continued)

OTHER PUBLICATIONS

Qiao et al., "Can Interventional Ablation be Applied to the Treatment of Arterial Aneurysm?," Medical Hypotheses, vol. 80, No. 4, Apr. 2013, pp. 373-375.
(Continued)

*Primary Examiner* — Khadijeh A Vahdat
(74) *Attorney, Agent, or Firm* — Shumaker & Sieffert, P.A.

(57) ABSTRACT

In examples, a cold therapy system includes an intravascular medical device and a therapeutic medical device. The intravascular medical device includes a cold therapy assembly and an elongated member. The cold therapy assembly includes one or more surfaces configured to remove heat from the wall of the vessel. The elongated member is coupled to the cold therapy assembly. The therapeutic medical device is communicatively coupled to the cold therapy assembly and is configured to control the cold therapy assembly to ablate smooth muscle cells of the wall of the vessel without substantially denaturating one or more structural proteins of the wall of the vessel.

24 Claims, 10 Drawing Sheets

(56) References Cited

U.S. PATENT DOCUMENTS

| | | | |
|---|---|---|---|
| 6,468,297 | B1 | 10/2002 | Williams et al. |
| 6,537,271 | B1 | 3/2003 | Murray et al. |
| 6,575,966 | B2 | 6/2003 | Lane et al. |
| 6,610,083 | B2 | 8/2003 | Keller et al. |
| 6,893,433 | B2 | 5/2005 | Lentz |
| 6,908,462 | B2 | 6/2005 | Joye et al. |
| 6,939,345 | B2 | 9/2005 | KenKnight et al. |
| 7,344,490 | B2 | 3/2008 | Shaw et al. |
| 8,012,147 | B2 | 9/2011 | Lafontaine |
| 8,048,067 | B2 | 11/2011 | Davalos et al. |
| 8,911,430 | B2 | 12/2014 | Hoey et al. |
| 8,968,282 | B2 | 3/2015 | Buchbinder et al. |
| 9,072,500 | B2 | 7/2015 | Duong et al. |
| 9,237,919 | B2 | 1/2016 | Maschke |
| 9,598,691 | B2 | 3/2017 | Davalos |
| 9,615,878 | B2 | 4/2017 | Nair |
| 9,937,332 | B2 | 4/2018 | Nahon et al. |
| 9,999,461 | B2 | 6/2018 | Azamian et al. |
| 10,085,802 | B2 | 10/2018 | Neuberger |
| 10,568,687 | B2 | 2/2020 | Chen et al. |
| 10,588,682 | B2 | 3/2020 | Kelly et al. |
| 2002/0169489 | A1 | 11/2002 | Dobak, III et al. |
| 2002/0173784 | A1 | 11/2002 | Sliwa et al. |
| 2005/0182365 | A1 | 8/2005 | Hennemann et al. |
| 2011/0257641 | A1 | 10/2011 | Hastings et al. |
| 2012/0065554 | A1 | 3/2012 | Pikus |
| 2012/0089047 | A1* | 4/2012 | Ryba ...................... A61B 18/02 600/300 |
| 2012/0095461 | A1 | 4/2012 | Herscher et al. |
| 2013/0190748 | A1 | 7/2013 | Coe et al. |
| 2013/0197555 | A1 | 8/2013 | Schaer |
| 2018/0353239 | A1 | 12/2018 | Stone et al. |
| 2019/0117301 | A1 | 4/2019 | Steinke et al. |
| 2019/0224484 | A1 | 7/2019 | Pierce et al. |
| 2020/0015886 | A1 | 1/2020 | Whayne et al. |
| 2020/0085482 | A1 | 3/2020 | Buchbinder et al. |
| 2020/0129220 | A1 | 4/2020 | Jung |
| 2020/0179045 | A1 | 6/2020 | Levin et al. |
| 2023/0165632 | A1 | 6/2023 | Tunev et al. |
| 2023/0165633 | A1 | 6/2023 | Hartman et al. |
| 2026/0123952 | A1* | 5/2026 | Warnking ...... A61B 17/320068 |

FOREIGN PATENT DOCUMENTS

| | | | |
|---|---|---|---|
| WO | 2017040371 | A1 | 3/2017 |
| WO | 2021209523 | A1 | 10/2021 |

OTHER PUBLICATIONS

PolarCath, Nucryo Vascular Inc., retrieved from www.nucryovasc.com/polarcath.html#polarcath_system, on May 17, 2021, 4 pp.

* cited by examiner

VESSEL MODIFICATION USING COLD THERAPY

This application claims the benefit of U.S. Provisional Application No. 63/284,358, filed on Nov. 30, 2021, and entitled, "VESSEL MODIFICATION USING COLD THERAPY," the entire content of which is incorporated herein by reference.

TECHNICAL FIELD

The present technology is related to intravascular medical devices, such as ablative medical devices.

BACKGROUND

Balloon angioplasty may be used to treat cardiovascular diseases involving abnormal constriction or enlargement of blood vessels, such as cerebrovascular disease, coronary heart disease, and peripheral arterial disease. These abnormal constrictions or enlargements may be caused by underlying tissue morphology near smooth muscle tissue lining the blood vessel wall, such as fatty plaques.

SUMMARY

The present disclosure describes devices, systems, and methods for delivery of cold therapy to a constricted vessel to modify a structure of the vessel, such as by enlarging the vessel, increasing an elasticity of the vessel, or stabilizing plaques within the vessel. In examples described herein, an intravascular medical device, such as a catheter, is configured to be positioned within a constricted vessel, such as a vessel that includes a build-up of plaque. A distal end of the intravascular medical device includes a cold therapy assembly configured to contact a wall of the vessel and remove heat from the wall of the vessel. A medical device coupled to the intravascular medical device is configured to control the amount of heat removed by the intravascular medical device to ablate smooth muscle cells of the wall of the vessel without substantially denaturing one or more structural proteins, such as elastin or collagen, in the wall of the vessel. For example, ablation of smooth muscle cells may occur at a lower cooling load, such as at a higher temperature or for a shorter therapy time, than denaturation of structural proteins, and an amount of heat removed by the intravascular medical device can be selected to ablate the smooth muscle cells and not denature at least some of the structural proteins (e.g., not denature a majority of the structural proteins).

After cold therapy, the smooth muscle cells may no longer provide a relatively high constricting force on an inner layer of the wall of the vessel, such that the vessel may have an increased diameter in response to fluid (e.g., blood) flow at certain pressures (e.g., blood pressure of the patient). However, the intact structural proteins of the wall of the vessel may continue to provide plasticity and elasticity to support the wall of the vessel. In this way, a constricted vessel may be expanded for a relatively long period of time without the use of long-term support devices or substances, such as stents or drugs.

In some examples, the intravascular medical device includes an expansion device, such as a balloon, a basket, a net, or other expansive structure, that may aid in modifying the structure of the vessel prior to or during cold therapy. For example, the expansion device may be configured to expand from a delivery configuration to a deployed configuration to increase the inner diameter of the vessel while the cold therapy assembly removes heat from the vessel. Such simultaneous expansion and therapy may further increase the diameter of the vessel post-therapy, which may provide therapeutic results to the patient.

In some examples, the disclosure describes a system that includes an intravascular medical device and a therapeutic medical device. The intravascular medical device a cold therapy assembly and an elongated member. The cold therapy assembly includes one or more surfaces configured to contact a wall of a vessel and remove heat from the wall of the vessel. The elongated member is coupled to the cold therapy assembly and configured to support and/or guide the cold therapy assembly to a treatment site. The therapeutic medical device is communicatively coupled to the cold therapy assembly and configured to control the cold therapy assembly to ablate smooth muscle cells of the wall of the vessel without substantially denaturating one or more structural proteins of the wall of the vessel.

In some examples, the disclosure describes a method that includes contacting a wall of a vessel with one or more surfaces of a cold therapy assembly. The wall of the vessel includes smooth muscle cells and one or more structural proteins. The method includes removing heat from the wall of the vessel to ablate the smooth muscle cells without denaturing the one or more structural proteins.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein.

DETAILED DESCRIPTION

Figure 1:
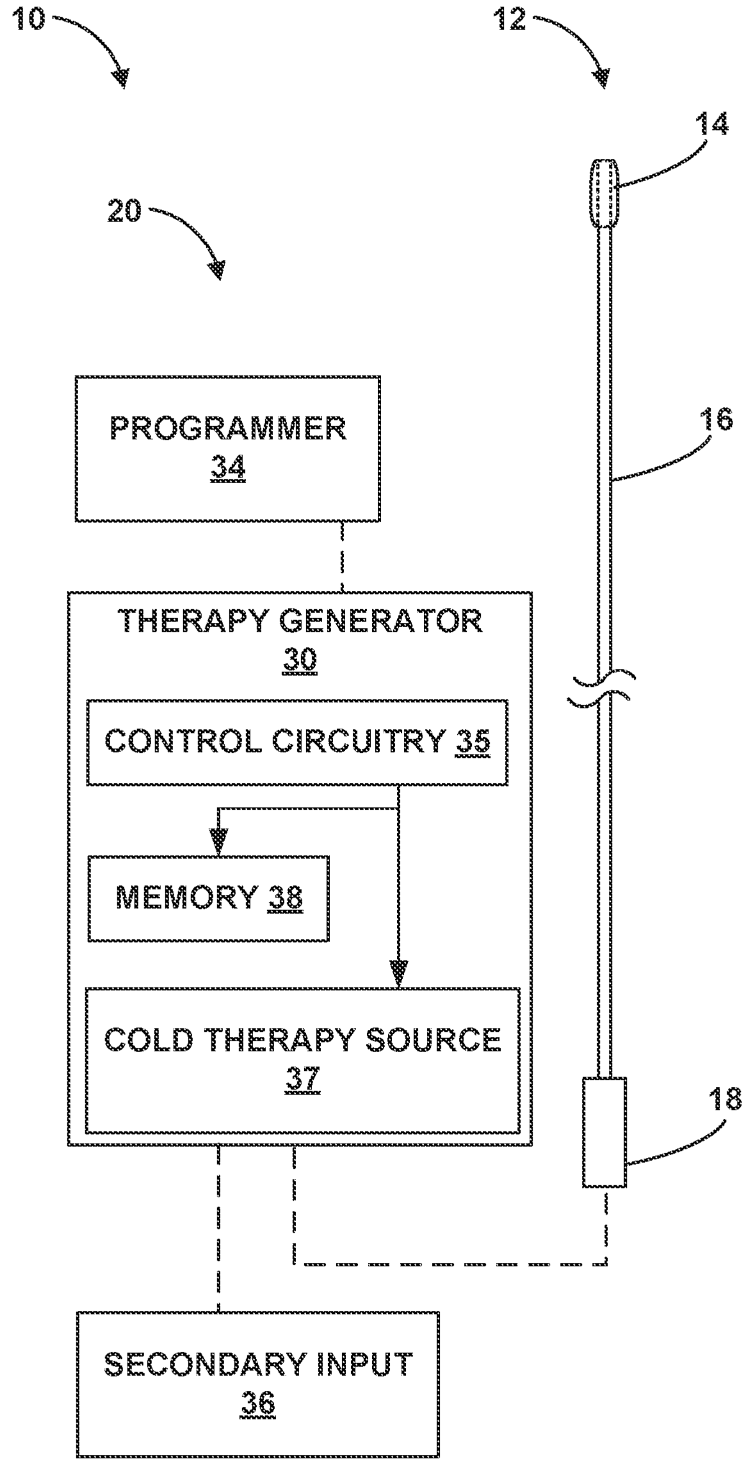
FIG. 1 is a partially schematic illustration of a vascular cold therapy system that includes an example intravascular medical device, in accordance with some examples of the present disclosure.

The present technology is directed to devices, systems, and methods for cryoablation of a constricted vessel.

As used herein, the terms “distal” and “proximal” define a position or direction with respect to the treating clinician or clinician’s control device (e.g., a handle assembly). “Distal” or “distally” can refer to a position distant from or in a direction away from the clinician or clinician’s control device. “Proximal” and “proximally” can refer to a position near or in a direction toward the clinician or clinician’s control device.

Balloon angioplasty may be used to treat cardiovascular diseases involving abnormal constriction of blood vessels. Two techniques to treat abnormal constrictions include plain old balloon angioplasty (POBA) and drug-coated balloon (DCB) angioplasty. In these techniques, a balloon catheter may be positioned in a vessel and expanded to widen the vessel. After deflation and removal of the balloon catheter, the blocked vessel may contract and reduce flow, as the plaques may remain on the walls of the vessel. In addition, after the pressure from the balloon is released, the muscle tissue of the vessel wall may rebound and the blood vessel may narrow relative to the expanded size. This may be referred to as elastic recoil.

To support the widened vessel, one or more additional treatment devices or substances may be applied to the walls of the vessel to maintain the widened vessel. As one example, a support structure (e.g., a stent) may be positioned in the widened vessel to help prevent constriction of the vessel. As another example, a drug may be impregnated into the wall of the vessel to inhibit healing of the tissues in the wall of the vessel following balloon expansion, and may further include one or more drugs to inhibit healing of the tissues. The support structure and/or drugs may result in certain complications, such as by creating a blockage, triggering an adverse reaction, or requiring complex procedures for supporting the vessel.

In accordance with examples of the current disclosure, a vascular cold therapy system includes an intravascular medical device configured to deliver cold therapy to a wall of a vessel to increase blood flow through the vessel without additional treatment devices or substances. The cold therapy can be referred to as cryoablation in some cases. The cold therapy delivered by the intravascular medical device is configured to remove heat from the wall of the vessel to reduce the temperature of tissues in the wall of the vessel. These tissues include living cells, such as smooth muscle cells and endothelial cells, that provide rigidity to the wall of the vessel, and structural proteins, such as elastin and collagen fibers, that provide elasticity and plasticity to the wall of the vessel. The temperature may be sufficiently low to ablate the smooth muscle cells and endothelial cells while leaving the structural proteins substantially intact. For example, a majority of the structural proteins (e.g., over 90%) in the portion of the vessel wall that is treated may be left intact. In response to regular blood pressure within the vessel, the wall of the vessel may expand to an increased cross-sectional area to the extent permitted by the continued support provided by the structural proteins, and eventually the endothelial and smooth muscle cells will grow back to the increased cross-sectional area. The structural proteins can, for example, function as scaffolding for the growth of the endothelial and smooth muscle cells. The resulting vessel may have reduced elastic recoil and/or increased flow without the use of support structures or drugs.

FIG. 1 is a partial schematic illustration of an example vascular cold therapy system 10 that includes an example therapy-applying intravascular medical device 12 and therapy-generating therapeutic medical device 20, in accordance with some examples of the present disclosure. Intravascular medical device 12 includes an elongated member 16 defining a longitudinal axis and configured to be positioned within vasculature of a patient. In some examples, intravascular medical device 12 includes a hub 18 coupled to a proximal portion of elongated member 16. Elongated member 16 and hub 18 are described in further detail below.

Elongated member 16 is configured to be navigated through vasculature of the patient, for example, to position a cold therapy assembly 14 adjacent a target treatment site of a vessel of the patient. For example, elongated member 16 may be used to access relatively distal vasculature locations in a patient or other relatively distal tissue sites (e.g., relative to a vasculature access point). Example vasculature locations may include, for example, locations in a coronary artery, peripheral vasculature (e.g., carotid, iliac, or femoral artery, or a vein), or cerebral vasculature. In some examples, elongated member 16 is structurally configured to be relatively flexible, pushable, and relatively kink- and buckle-resistant, so that it may resist buckling when a pushing force is applied to a relatively proximal portion of intravascular medical device 12 to advance elongated member 16 distally through vasculature, and so that it may resist kinking when traversing around a tight turn in the vasculature. Elongated member 16 may have any suitable shape, such as a tubular body or a paddle-like shape. Elongated member 16 may be constructed using any suitable materials. In some examples, elongated member 16 may include one or more polymeric materials, for example, polyamide, polyimide, polyether block amide copolymer sold under the trademark PEBAX, polyethylene terephthalate (PET), polypropylene, aliphatic, polycarbonate-based thermoplastic polyurethane, or a polyether ether ketone (PEEK) polymer that provides elongated member 16 with a predetermined flexibility. The polymeric materials may be extruded as one or more solid or hollow tubes to form elongated member 16.

In some examples, a support structure or shape member may be included within or about elongated member 16, for example, being disposed about, within, or between one or more polymeric tubes used to form elongated member 16. The support structure or shape member may be used to impart a predetermined strength, flexibility, shape, or geometric qualities to elongated member 16. The support structure or shape member may be formed using any suitable materials including, for example, metal, alloy, or polymer-based wires used to form coils or braids, a hypotube, shape memory materials, for example, nickel-titanium (nitinol), shape memory polymers, electro-active polymers, or the like. The support structure or shape member may be cut using a laser, electrical discharge machining (EDM), electrochemical grinding (ECG), or other suitable means to achieve a desired finished component length, apertures, and geometry. In some examples, the support structure or shape member may be arranged in a single or dual-layer configuration, and manufactured with a selected tension, compression, torque and pitch direction.

Elongated member 16 may also include one or more radiopaque markers which may help a clinician determine the positioning of elongated member 16, e.g., cold therapy assembly 14 or a distal end of elongated member 16, relative to relative to the target treatment site using ultrasound or other suitable technique. For example, one or more radiopaque markers may be positioned along elongated member 16 such as near a distal end, adjacent to cold therapy assembly 14 or the like.

In some examples, at least a portion of an outer surface of elongated member 16 may include one or more coatings, such as, but not limited to, an anti-thrombogenic coating, which may help reduce the formation of thrombi in vitro, an anti-microbial coating, and/or a lubricious coating. In some examples, the entire working length of elongated member 16 may be coated with the hydrophilic coating. In other examples, only a portion of the working length of elongated member 16 coated with the hydrophilic coating. This may provide a length of elongated member 16 distal to hub 18 with which the clinician may grip elongated member 16, e.g., to rotate elongated member 16 or push elongated member 16 through vasculature. In some examples, the entire working length of elongated member 16 or portions thereof may include a lubricious outer surface, e.g., a lubricious coating. The lubricating coating may be configured to reduce static friction and/or kinetic friction at a surface of elongated member 16 as elongated member 16 is advanced through the vasculature.

The proximal portion of elongated member 16 may be received within hub 18 and can be mechanically connected to hub 18 via an adhesive, welding, or another suitable technique or combination of techniques. Hub 18 may serve as a handle for intravascular medical device 12 allowing the clinician to grasp intravascular medical device 12 at hub 18 and advance elongated member 16 through vasculature of a patient. In some examples, intravascular medical device 12 can include another structure in addition or instead of hub 18. For example, intravascular medical device 12 or hub 18 may include one or more luers or other mechanisms (e.g., access ports) for establishing connections between intravascular medical device 12 and other devices. Additionally, or alternatively, intravascular medical device 12 may include a strain relief body (not shown), which may be a part of hub 18 or may be separate from hub 18 to alleviate potential strain of kinking of elongated member 16 near its proximal end.

Intravascular medical device 12 includes cold therapy assembly 14. Cold therapy assembly 14 is mechanically connected to and carried by elongated member 16. In some examples, such as illustrated in FIG. 1, cold therapy assembly 14 is positioned at a distal portion of elongated member 16; in other examples, cold therapy assembly 14 may be positioned elsewhere on elongated member 16. Cold therapy assembly 14 is configured to position within a vessel, such as at a wall of the vessel (e.g., contacting the wall of the vessel) or proximate to the wall of the vessel (e.g., within a threshold distance to remove heat through a fluid, such as blood). For example, cold therapy assembly 14 may include, or be coupled to, an expansion structure configured to expand from a radially collapsed delivery configuration to a radially expanded deployed configuration. In the deployed configuration, one or more surfaces of cold therapy assembly 14 may be positioned in thermal communication with the wall of the vessel, such that the one or more surfaces may direct (e.g., contacting) or indirectly (e.g., via a fluid or other medium) remove heat from the wall of the vessel. In some examples, cold therapy assembly 14 and/or an expansion structure coupled to cold therapy assembly 14 may be configured to expand beyond an initial diameter of the vessel, such that surfaces of cold therapy assembly 14 may be in thermal communication with the wall of the vessel while the vessel is expanded beyond the initial diameter of the vessel.

Cold therapy assembly 14 is configured to deliver cold therapy to a vessel, such as a constricted vessel, by removing heat from the wall of the vessel. Cold therapy assembly 14 may remove heat from the vessel using any of a variety of heat removal mechanisms. In some examples, such as illustrated in FIGS. 3A-3C and 5A-5C, cold therapy assembly 14 defines a cavity configured to contain a thermal medium, such as a cooled gaseous or liquid fluid, a phase change fluid, or endothermic reactants and/or products. In some examples, such as illustrated in FIGS. 4A-4C and 5D, cold therapy assembly 14 includes one or more therapeutic elements configured to change temperature in response to an electric voltage, such as thermoelectric elements. The thermal medium and/or plurality of therapeutic elements may create a temperature differential between one or more surfaces of cold therapy assembly 14 and the wall of the vessel, such that heat may transfer from the wall of the vessel to the thermal medium and/or the one or more therapeutic elements.

Therapeutic medical device 20 includes a therapy generator 30 configured to be coupled to cold therapy assembly 14, such as through hub 18. Therapy generator 30 is configured to control cold therapy assembly 14 to remove heat from the wall of the vessel to ablate smooth muscle cells of the wall of the vessel without substantially denaturing one or more structural proteins (e.g., such as elastin and/or collagen fibers) of the wall of the vessel. Structural proteins, such as elastin or collagen, are wavy fibers that can straighten under small loads, allowing large extension of the tissue at low stress. Cold denaturation of structural proteins may cause protein unfolding and loss of hydrogen bonds, resulting in reduction in structural properties, such as elasticity or plasticity, of the structural proteins, such as due to degradation or fragmentation. Substantial denaturation of the structural proteins may involve denaturation beyond natural processes (e.g., due to elastase or collagenase), and may result in greater than about 50% of structural proteins in a volume of tissue (e.g., one or more layers of the wall of the vessel) degrading or fragmenting. On the other hand, not substantially denaturing structural proteins may result in less than about 50% by volume of structural proteins in a volume of tissue degrading or fragmenting, such as less than about 10%. Smooth muscle cells are living cells that maintain a diameter of a vessel. Ablation of smooth muscle cells may include reduction in structural properties, such as rigidity, of the smooth muscle cells, such as due to lysis or rupture of the smooth muscle cells. Substantial ablation of the smooth muscle cells may involve ablation beyond natural processes (e.g., due to cell replacement), and may result in greater than about 50% of smooth muscle cells in a volume of tissue (e.g., one or more layers of the wall of the vessel) lysing or rupturing, such as greater than about 90%. In some examples, denaturation of structural proteins and/or ablation of smooth muscle cells may be measured by a change in thickness of one or more layers of the wall of the vessel having the structural proteins and/or smooth muscle cells. Effects of cold therapy on ablation of smooth muscle cells and denaturation of structural proteins will be described further in FIGS. 2A-2E below.

Therapy generator 30 includes a cold therapy source 37 configured to cause cold therapy assembly 14 to deliver cold therapy that may provide therapeutic benefits to a patient. In some examples, such as examples in which cold therapy assembly 14 includes one or more therapeutic elements, cold therapy source 37 includes an electrical energy source configured to apply a voltage to the therapeutic elements to reduce a temperature of the therapeutic elements. In some examples, such as examples in which cold therapy assembly 14 defines a cavity configured to contain a thermal medium, cold therapy source 37 includes a fluid source configured to deliver the thermal medium to the cavity of cold therapy assembly 14. In such examples, generator 30 may be configured to generate a selected rate and/or magnitude of cold therapy delivered by cold therapy source 37 to the target treatment site via cold therapy assembly 14. For example, generator 30 may include control circuitry 35 configured to control a flow rate, amount, temperature, and/or pressure of fluid delivered by cold therapy source 37 or an amount of voltage applied by cold therapy source 37.

Generator 30 may include a memory 38. Memory 38 includes computer-readable instructions that, when executed by control circuitry 35, causes generator 30 to perform various functions. Control circuitry 35 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to control circuitry 35 herein may be embodied as software, firmware, hardware or any combination thereof. Memory 38 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 38 may store any suitable information, including patient identification information, and information for selecting the rate and/or magnitude of cold therapy which generator 30 generates and delivers to a patient via cold therapy assembly 14. Memory 38 may also store operating instructions with which control circuitry 35 controls the operation of generator 30.

System 10 may include a programmer 34, which includes circuitry configured to communicate with generator 30 and control an operation of generator 30. For example, generator 30 can be configured to receive one or more cold therapy parameter values with which generator 30 generates and delivers fluid and/or power to cold therapy assembly 14 via programmer 34. In some examples, generator 30 or programmer 34 may include one or more evaluation or feedback modules to provide feedback to the clinician before, during, and/or after cold therapy, such as lights, a display, sound generating circuitry, or the like or combination thereof. Generator 30 or programmer 34 may include a user interface configured to receive user input from a user, e.g., one or more cold therapy parameter values with which control circuitry 35 controls cold therapy source 37, input to control when (e.g., on/off/pause control) generator 30 is applying cold therapy to a cold therapy assembly 14, or the like.

In some examples, one or more sensors (not shown) configured to sense a parameter related to the cold therapy, such as one or more temperature (for example, thermocouple, thermistor, or the like), impedance, pressure, optical, flow, ultrasound or SONAR (e.g. for the detection of ice penetration depth), chemical or other sensors, may be located proximate to or within cold therapy assembly 14 and connected to one or more electrical conductors (not shown) within elongated member 16. Generator 30 may be part of a device or monitor that may include processing circuitry, such as a microprocessor, and a display. Control circuitry 35 or control circuitry of another device, such as programmer 34, may receive one or more signals indicative of the one or more sensed parameters and control cold therapy source 37 based on the signal.

In some examples, functions described with reference to generator 30 may be performed by programmer 34. Thus, in some examples, programmer 34 may include a memory (for example, in generator 30 or programmer 34), and control circuitry coupled to the memory.

A secondary input 36, such as a foot pedal, may be connected (e.g., pneumatically connected or electrically connected) to generator 30 to enable the clinician to initiate, terminate and, optionally, adjust various operational characteristics of generator 30, including, but not limited to, fluid delivery or power delivery. System 10 may also include a remote control device (not shown) that can be positioned in a sterile field and operably coupled to one or both of intravascular medical device 12 or generator 30. In other examples, the remote control device may be built into hub 18.

Figure 2A:
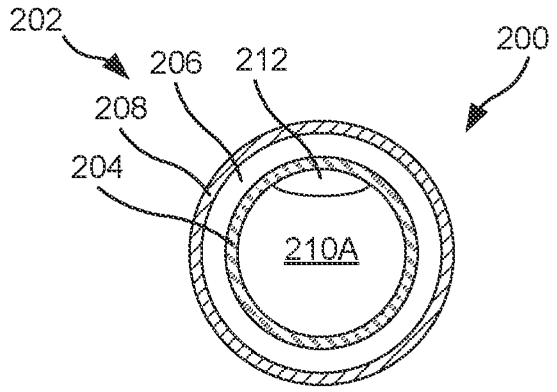
FIG. 2A is a cross-sectional illustration of an example artery.

Cold therapy systems described herein may be used to apply cold therapy for treatment of any of a variety of conditions for which cold therapy delivered to a wall of a vessel may provide therapeutic benefits. Such cold therapy may be particularly beneficial for treating constricted vessels or increasing systemic blood volume to reduce systemic blood pressure. As one example, a vessel, such as an artery, may be narrowed or otherwise constricted due to build-up of plaque or other tissue in the vessel. As another example, while a vessel may otherwise be a regular size, the systemic blood pressure of the patient may nonetheless be high, such that enabling the blood vessel to enlarge may reduce the systemic blood pressure. FIG. 2A is a cross-sectional illustration of an example artery 200. Artery 200 includes an artery wall 202 defining an artery lumen 210A. Artery wall 202 includes various layers, including an inner tunica intima 204, an intermediate tunica media 206, and an outer tunica adventitia 208. Tunica intima 204 includes endothelial cells and, in certain arteries, an elastic sheath and/or smooth muscle cells. The endothelial cells may form an interface between wall 202 and blood flowing in lumen 210A. Tunica media 206 includes smooth muscle cells and structural proteins, such as elastin and collagen fibers. The smooth muscle cells may provide rigid support to wall 202, as well as an ability to constrict or relax artery 200, and thus assist in regulation of blood flow and pressure, and the structural proteins may provide plasticity and elasticity to wall 202. Tunica adventitia 208 also includes structural proteins, which may perform a similar function as structural proteins of tunica media 206.

Artery 200 may also include plaque 212 or fatty tissues deposited on an inner surface of wall 202. Plaque 212 may deposit over time and constrict a cross-sectional area of lumen 210A. In other examples, artery 200 (or other vessel) may not be constricted due to plaque 212 or another blockage, or such blockage may be unknown. For example, cold therapy may be provided to artery 200 as a preventative therapy, such as if an angiogram indicates an obstruction, but no clinical signs of blockage are detected, such that a clinician can deliver the cold therapy as a prophylactic measure.

Prior to cold therapy, a cross-sectional area of lumen 210A (taken in a plane orthogonal to a longitudinal axis of artery 200) may be a function of a structure of wall 202 and a presence of any deposits, such as plaque 212, on the inner surface of wall 202. Plaque 212 may be difficult to remove, and debris from plaque 212 may form clots downstream of plaque 212. Regenerative cells of wall 202, such as endothelial cells of tunica intima 204, and non- or less-regenerative cells of wall 202, such as smooth muscle cells of tunica media 206, may provide rigidity to wall 202, such as by resisting radially outward forces on an inner surface of wall 202 by blood flow and radially inward forces on an outer surface of wall 202 by adjacent tissues. Structural proteins of wall 202, such as structural proteins of tunica media 206 and tunica adventitia 208, may provide plasticity and elasticity to wall 202, such as by expanding in response to radially outward forces on an inner surface of wall 202 by blood flow in lumen 210A and conforming to a balance of radially inward and outward forces on walls 202.

Figure 2B:
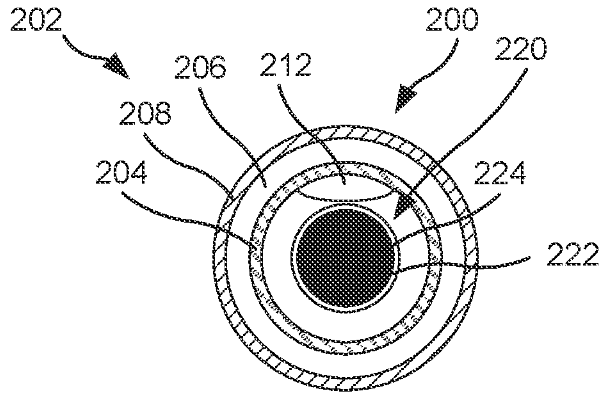
FIG. 2B is a cross-sectional illustration of the artery of FIG. 2A under expansion from an intravascular medical device, in accordance with some examples of the present disclosure.

FIG. 2B is a cross-sectional illustration of artery 200 of FIG. 2A including an intravascular medical device 220 at least partially positioned within artery 200, in accordance with some examples of the present disclosure. A distal end of intravascular device 220 is positioned within artery 200 near a treatment site, such as a constricted section of artery 200 near plaque 212. Device 200 is an example of device 200 of FIG. 2B. The distal end of intravascular medical device 220 includes a cold therapy assembly 222 and an elongated body 224, such as cold therapy assembly 14 and elongated member 16, respectively, of FIG. 1. Intravascular medical device 220, cold therapy assembly 222, and elongated body 224 are examples of intravascular medical device 12, cold therapy assembly 14, and elongated body 16 of FIG. 1. In the example of FIG. 2B, cold therapy assembly 222 includes an expansion device, such as a balloon or an expandable basket, configured to expand and cause one or more surfaces of cold therapy assembly 222 to contact an inner surface of wall 202. However, in other examples, intravascular medical device 220 may include an expansion device separate from surfaces of cold therapy assembly 222 configured to wall 202.

Figure 2C:
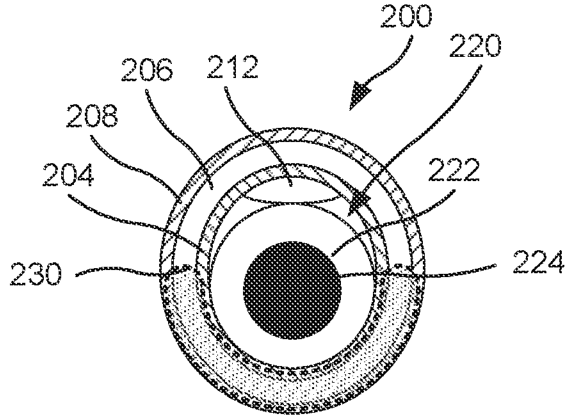
FIG. 2C is a cross-sectional illustration of the artery of FIG. 2A under cold therapy from an intravascular medical device, in accordance with some examples of the present disclosure.

FIG. 2C is a cross-sectional illustration of artery 200 of FIG. 2A receiving cold therapy from intravascular medical device 220, in accordance with some examples of the present disclosure. Intravascular medical device 220 is in a deployed configuration, such that one or more surfaces of cold therapy assembly 222 contact an inner surface of wall 202. In the example of FIG. 2C, an outer surface of cold therapy assembly 222 is contacting about half (e.g., 40-60%, or 45-55%) of an inner surface of wall 202 and an inwardly-facing surface of plaque 212, and has expanded a perimeter of the inner surface of wall 202.

Cold therapy assembly 222 is configured to remove heat from wall 202 to create a cold therapy region 230 of wall 202. Cold therapy region 230 may be a portion of wall 202 that includes tissues having a temperature in a target therapy temperature range. As will be described further below, a size and shape of cold therapy region 230 may depend on a variety of thermal properties of tissues of wall 202 and thermal parameters of cold therapy assembly 222, such as a distance of tissues or wall 202 from cold therapy assembly 222, a heat capacity of tissues of wall 202, a cooling load delivered by cold therapy assembly 222, and/or other properties and parameters that may influence an amount of heat that is transferred from tissues of wall 202 to cold therapy assembly 222.

The therapy temperature range of tissues in cold therapy regions 230 may include an upper therapy threshold value at which living cells, such as endothelial cells and/or smooth muscle cells, substantially ablate (e.g., greater than about 90% of smooth muscle cells ablated) but structural proteins, such as elastin and collagen, remain substantially intact (e.g., less than about 10% of elastin and collagen denatured). For example, without being limited to any particular theory, endothelial cells and smooth muscle cells must have intact cell membranes that primarily consist of lipids and proteins. Temperatures below an upper therapy threshold value may cause ice crystals to form in the cell membranes, causing rupture of the cell membrane and death of the cell. Structural proteins, such as elastin and collagen, are not living cells and are less affected by temperatures at which living cells begin to ablate. Temperatures below a lower therapy threshold value may cause proteins to begin to denature; however, this lower therapy threshold value is substantially lower than the temperature at which living cells begin to ablate. As such, cold therapy region 230 may be maintained at a temperature below the upper therapy threshold value and above the lower therapy threshold value for a period of time sufficient to substantially ablate the living cells of wall 202, such as in tunica intima 204 and tunica media 206, but substantially leave intact the structural proteins of wall 202, such as in tunica media 206 and tunica adventitia 208. In some instances, cold therapy assembly 222 may also remove heat from plaque 212A to further stabilize plaque 212. For example, low temperatures may contract plaque 212A and make plaque 212 less likely to rupture. In some examples, cold therapy region 230 is configured to limit cold therapy to other tissues outside artery 200. For example, a cooling load applied to artery 200 from cold therapy assembly 222 may form cold therapy region 230 such that tissues adjacent to wall 202 of artery 200, such as nerves or other tissues, may not be substantially ablated (e.g., less than about 10% ablation) or be substantially cooled (e.g., cooled to less than about 0° C.).

Figure 2D:
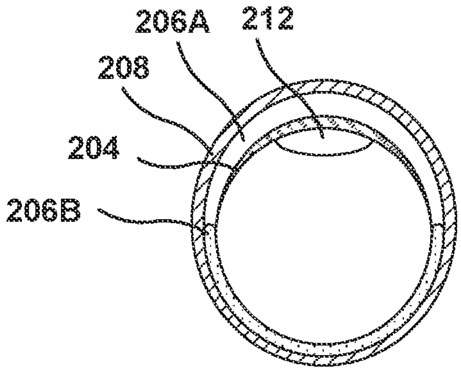
FIG. 2D is a cross-sectional illustration of the artery of FIG. 2A immediately after cold therapy from an intravascular medical device, in accordance with some examples of the present disclosure.

FIG. 2D is a cross-sectional illustration of artery 200 of FIG. 2A after (e.g., immediately after) cold therapy from intravascular medical device 220, in accordance with some examples of the present disclosure. As a result of ablation of endothelial cells of tunica intima 204, tunica intima 204 includes a partially intact endothelial lining. Tunica media 206 includes an intact portion 206A that was not subject to cold therapy region 230 and includes smooth muscle cells, and an ablated portion 206B that was subject to cold therapy region 230 and does not include smooth muscle cells. Without smooth muscle cells, ablated portion 206B of tunica media 206 may be more plastic and elastic than tunica media 206 prior to cold therapy, such that tunica media 206 may expand to a greater extent in response to normal blood pressure than prior to cold therapy. In some instances, ablated portion 206B may have reduced recoil due to a reduction or absence of smooth muscle cells.

Although plaque 212 is shown in FIG. 2D as having a similar configuration as that shown in FIG. 2A with respect to the pre-expanded state of vessel 200, in some cases, the expansion of the expansion device may cause plaque 212 to move radially outwards.

Figure 2E:
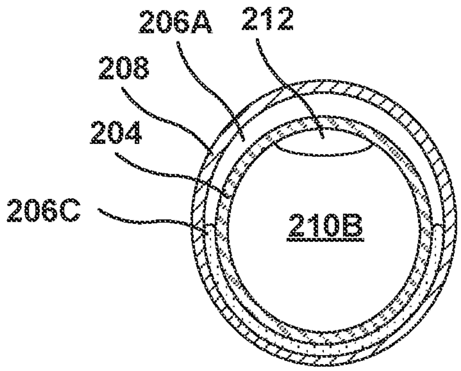
FIG. 2E is a cross-sectional illustration of the artery of FIG. 2A several weeks after cold therapy from an intravascular medical device, in accordance with some examples of the present disclosure.

FIG. 2E is a cross-sectional illustration of artery 200 of FIG. 2A several weeks after cold therapy from intravascular medical device 220, in accordance with some examples of the present disclosure. Healed portion 206C of tunica media 206 may include some scar tissue; however, such scar tissue may be less present than a tunica media in which structural proteins had been damaged. Endothelial cells of tunica intima 204 have grown back on an expanded ablated portion 206B of tunica media 206. As a result, lumen 210B may have a greater cross-sectional area after cold therapy than lumen 210A prior to cold therapy. While lumen 210B is shown as having a substantially circular cross-section, lumen 210B may have a variety of shapes. For example, due to reduced support of tunica media 206, a portion of wall 202 may be more influenced by surrounding tissues and blood pressure within lumen 210B than prior to ablation of the smooth muscle cells. However, a force applied to an inner surface of wall 202 may generally be greater than a force applied to an outer surface of wall 202, such that lumen 210B may have a greater cross-sectional area under normal blood pressure than lumen 210A prior to cold therapy.

While FIGS. 2A-2E have been described with respect to expanding a constricted artery, in some examples, intravascular medical devices described herein may be used to increase blood volume and reduce systemic blood pressure. For example, renal arteries or other vessels may be modified to expand and handle a greater blood volume in response to blood pressure, thereby lowering the systemic blood pressure of a patient, regardless of whether the vessel has been constricted from a higher initial diameter. A cold therapy assembly, such as cold therapy assembly 222, may be positioned in thermal communication with a treatment site of a renal artery and operated to remove heat from the wall of the renal artery. As a result, the renal artery may expand under blood pressure of the patient, thereby reducing the systemic blood pressure of the patient. In some examples, this treatment may be repeated at various positions within vessels of the patient.

Intravascular medical devices described herein, such as intravascular medical device 12 of FIG. 1, may include one or more of a variety of cold therapy assemblies having various mechanisms for extending one or more surfaces to contact a vessel and various mechanisms for removing heat from the vessel. In some examples, such as FIGS. 3A-3C, a cold therapy assembly includes a closed expansion device having an expandable cavity, such as a balloon, configured to contain a thermal medium within the cavity. The thermal medium may remove heat from the wall of the vessel through one or more surfaces of the closed expansion device. This bulk heat removal may provide a relatively even amount of heat removal to a large surface area of the vessel. FIGS. 3A-4C illustrate examples of intravascular medical device 12.

Figure 3A:
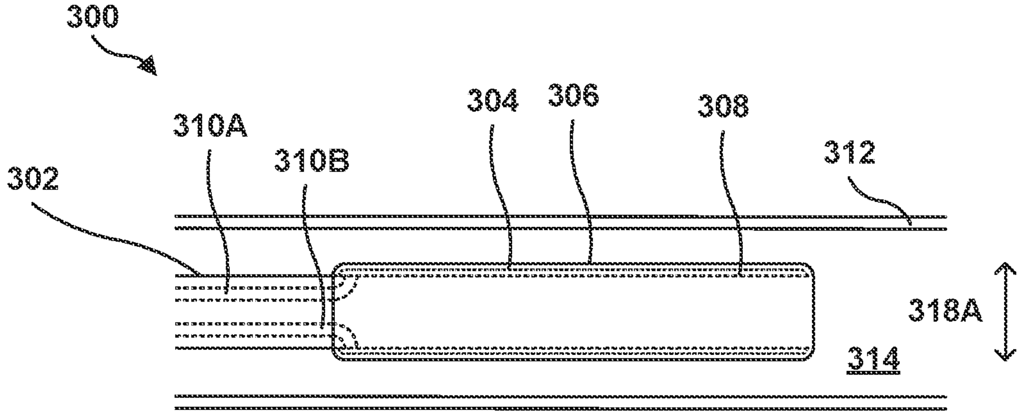
FIG. 3A is an expanded side view conceptual illustration of a distal portion of an example intravascular medical device positioned in a vessel in a delivery configuration.

FIG. 3A is an expanded side view conceptual illustration of a distal portion of an intravascular medical device 300 positioned in a lumen 314 of a vessel 312 in a delivery configuration. Intravascular medical device 300 includes a balloon 304 having an outer surface 306 and defining a cavity 308. When cold therapy assembly 300 is in a delivery configuration, such as illustrated in FIG. 3A, balloon 304 may be in a deflated configuration in which cavity 308 is empty or nearly empty, such that cold therapy assembly 300 may be navigated through vasculature and positioned within lumen 314 of vessel 312 proximate to a treatment site. For example, balloon 304 may have a diameter 318A that corresponds to or is slightly larger than a diameter of an elongated body 302 of intravascular medical device 302.

Intravascular medical device 300 includes elongated member 302, such as elongated member 16 of FIG. 1. Elongated member 302 includes one or more fluid channels 310A and 310B (individually and collectively "fluid channel 310" and "fluid channel 310," respectively). Each fluid channel 310 is configured to discharge a fluid into and/or discharge a fluid from cavity 308 of balloon 304. In the example of FIG. 3A, elongated member 302 includes a fluid inlet channel 310A configured to discharge a fluid into cavity 308 and a fluid outlet channel 310B configured to discharge the fluid from cavity 308; however, in other examples, elongated member 302 may include a single channel 310, additional channels 310, or channels 310 configured to discharge the fluid both to and from cavity 308. Fluid inlet channel 310A and fluid outlet channel 310B may each be in fluid communication with a fluid source through a port on a hub, such as hub 18 of FIG. 1.

Figure 3B:
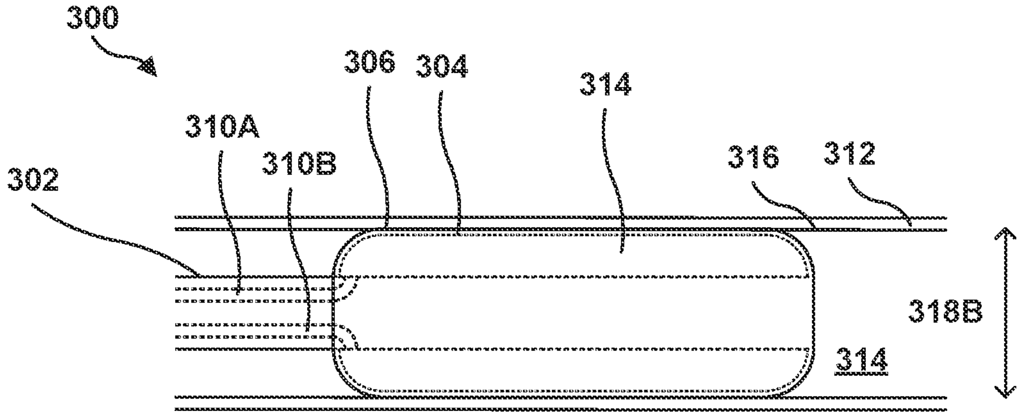
FIG. 3B is an expanded side view conceptual illustration of the distal portion of the example intravascular medical device of FIG. 3A positioned in the vessel in a deployed configuration.

FIG. 3B is an expanded side view conceptual illustration of a distal portion of example intravascular medical device 300 of FIG. 1 positioned in lumen 314 of vessel 312 in a first deployed configuration. Balloon 304 is configured to expand from the deflated configuration in the delivery configuration of intravascular medical device 300 to an inflated configuration in the first deployed configuration of intravascular medical device 300 in response to a pressure differential between an internal pressure within cavity 308 and an external pressure at outer surface 306, such that at least a portion of outer surface 306 of balloon 304 contacts and is in thermal communication with vessel 312. The internal pressure within cavity 308 may be sufficient such that at least a portion of outer surface 306 contacts a treatment site of vessel 312.

To increase an internal pressure within cavity 308 to expand balloon 304, cavity 308 is configured to receive and contain a pressurized fluid. In some examples, balloon 304 is configured to expand in response to cavity 308 being filled with the pressurized liquid. For example, balloon 304 may be configured to receive a pressurized cooling liquid through fluid inlet channel 310A that fills cavity 308 and expands to a particular pressure of the pressurized cooling liquid. In some examples, balloon 304 is configured to expand in response to cavity 308 being at least partially filled with a pressurized gas. As one example, balloon 304 may be configured to receive a pressurized liquid through fluid channel 310A and expand in response to the pressurized liquid expanding to a lower pressure gas in cavity 308. As another example, balloon 304 may be configured to receive a first reactant and expand as an endothermic reaction between the first reactant and a second reactant produces a gaseous product. Various example mechanisms for expanding a balloon will be discussed further in FIGS. 5A-5D below. As a result of expansion of balloon 304, outer surface 306 of balloon 304 may contact an inner surface of a wall of vessel 312, such that outer surface 306 is in thermal communication with the wall of vessel 312. For example, balloon 304 may have a first inflated diameter 318B greater than diameter 318A of FIG. 3A that corresponds to an inner diameter of vessel 312.

Cavity 308 is configured to receive and contain a thermal medium to remove heat from vessel 312. The thermal medium may include the pressurized fluid used to expand balloon 304, or may be a different medium within cavity 308 in addition to the pressurized fluid. The thermal medium may include one or more solids or fluids configured to remove heat from balloon 304 and, as a result, remove heat from a portion of vessel 312 in contact with outer surface 306 of balloon 304. When balloon 304 is in the expanded configuration, outer surface 306 includes one or more surfaces in contact with the wall of vessel 312 that receive heat flux from vessel 312 and transfer the heat flux through a wall of balloon 304 to the thermal medium within cavity 308. A thickness of balloon 304 between outer surface 306 and cavity 308 may be sufficiently low that balloon 304 may have a relatively small temperature gradient between outer surface 306 and an inner surface of balloon 304 defining cavity 308.

In some examples, balloon 304 includes one or more metallic elements configured to transfer heat from the wall of the vessel to the thermal medium. For example, balloon 304 may include thermally conductive particles dispersed in an elastomer, such that a wall of balloon 304 has increased thermal conductivity compared to balloons that do not include conductive thermally particles. As another example, balloon 304 may include one or more metallic elements on an inner or outer surface 306 of balloon 304 configured to aid in transfer of heat from outer surface 306 to the thermal medium in cavity 308, such as by increasing a thermal conductivity, and therefore heat flux, across the wall of balloon 304.

Figure 3C:
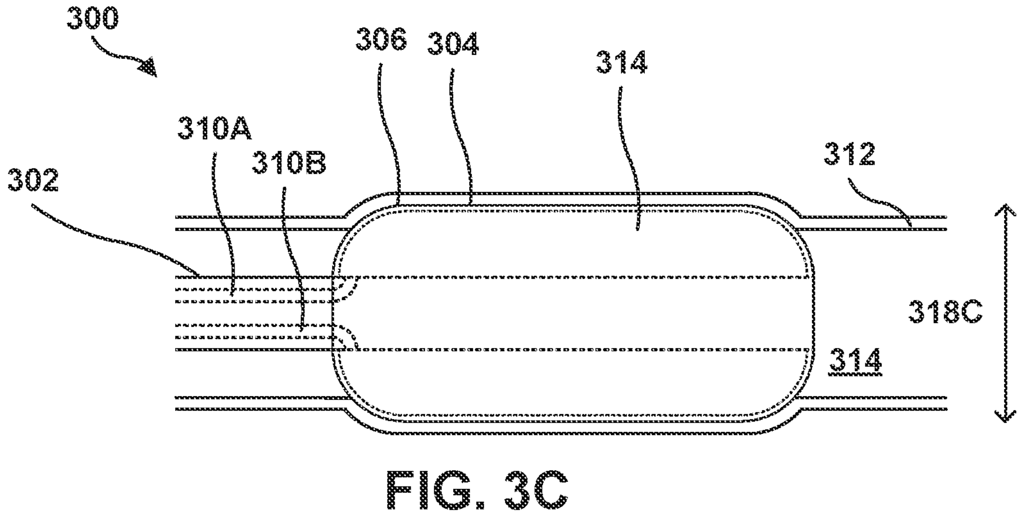
FIG. 3C is an expanded side view conceptual illustration of the distal portion of the example intravascular medical device of FIG. 3A positioned in the vessel in an expanded configuration.

In the example of FIG. 3B, balloon 304 is expanded to an internal diameter of vessel 312. However, in some examples, balloon 304 may be expanded beyond an initial diameter of vessel 312. For example, delivery of cold therapy to a vessel expanded beyond an initial diameter may further result in the vessel having a larger resulting diameter, thereby restoring blood flow. FIG. 3C is an expanded side view conceptual illustration of a distal portion of an example intravascular medical device positioned in an artery in second deployed configuration. In the second deployed configuration, an internal pressure of cavity 308 is sufficiently high to expand vessel 312 to a second inflated diameter 318C that is greater than first inflated diameter 318B. This larger, second inflated diameter 318C may help reduce recoil in vessel 312 and/or may increase a diameter at which remaining structural proteins of vessel 312 recoil. After the pressure from balloon 304 is released, vessel 312 may rebound to a larger diameter compared to a vessel that has not been expanded to an increased diameter prior to cold therapy.

Figure 4A:
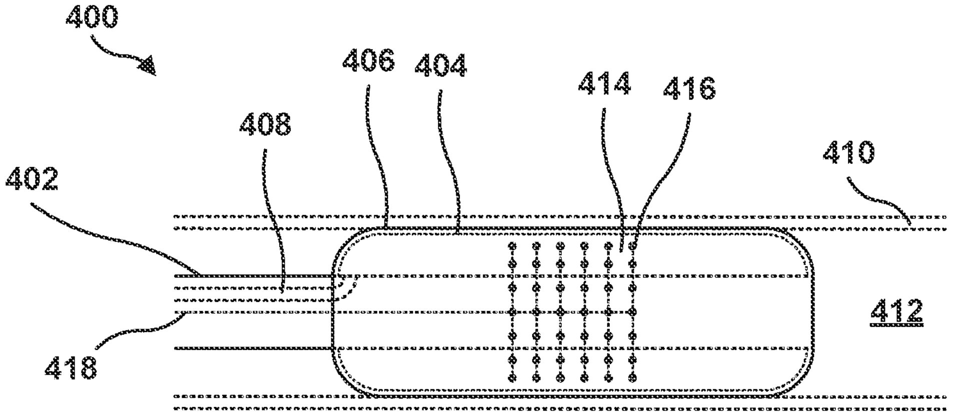
FIG. 4A is an expanded side view conceptual illustration of a distal portion of an example intravascular medical device configured to remove heat from a vessel wall using therapeutic elements on a balloon structure, in accordance with some examples of the present disclosure.
Figure 4B:
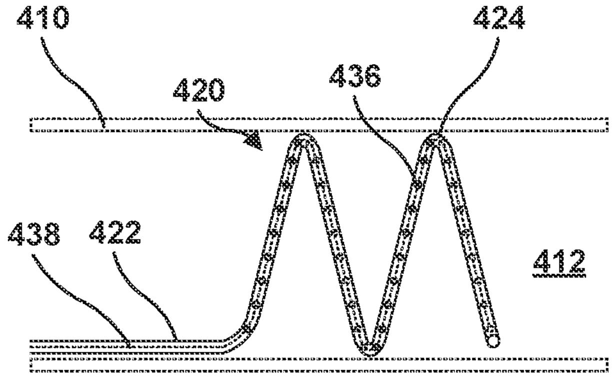
FIG. 4B is an expanded side view conceptual illustration of a distal portion of an example intravascular medical device configured to remove heat from a vessel wall using therapeutic elements on a spiral structure, in accordance with some examples of the present disclosure.
Figure 4C:
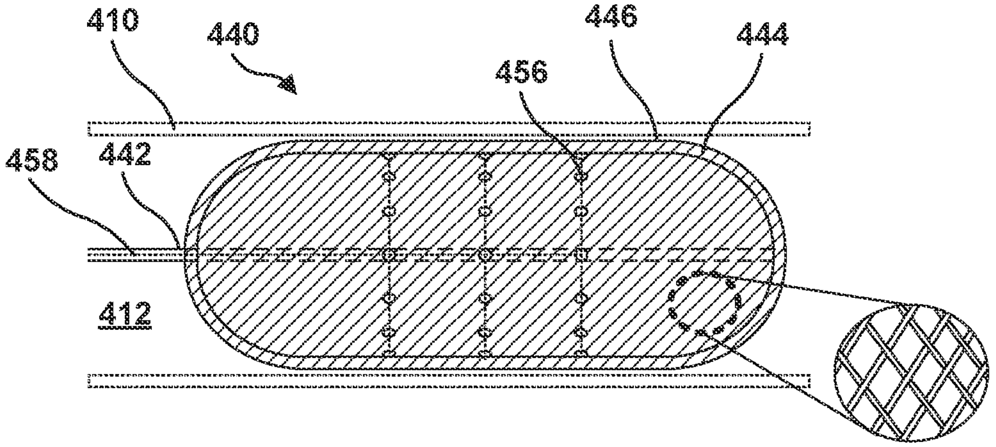
FIG. 4C is an expanded side view conceptual illustration of a distal portion of an example intravascular medical device configured to remove heat from a vessel wall using therapeutic elements on a net structure, in accordance with some examples of the present disclosure.

In some examples, such as FIGS. 4A-4C, a cold therapy assembly may include one or more discrete therapeutic elements coupled to an expansion device. The therapeutic elements may be configured to remove heat from the wall of the vessel through one or more surfaces of the therapeutic elements. This more localized heat removal may provide a configurable delivery of heat removal to surfaces of the vessel at particular axial and/or circumferential positions.

In some examples, intravascular medical devices described herein may include a balloon or other closed expansion structure as an expansion device for contacting a plurality of therapeutic elements against a wall of a vessel. FIG. 4A is an expanded side view conceptual illustration of a distal portion of an example intravascular medical device 400 configured to remove heat from a vessel 410 using therapeutic elements on a balloon 404, in accordance with some examples of the present disclosure. Intravascular medical device 400 includes balloon 404 coupled to an elongated body 402, such as elongated member 16 of intravascular medical device 12 of FIG. 1. Balloon 404 defines a longitudinal axis and is configured to be positioned within vessel 410 of a patient. Balloon 404 may be configured to switch between a delivery configuration, in which the expansion device 404 is deflated, to a deployed configuration as shown, in which balloon 404 is inflated. In the deployed configuration, balloon 404 may define a perimeter that extends along an inner surface of vessel 410, such that a plurality of therapeutic elements 416 at an outer surface of balloon 404 may contact the inner surface of vessel 410. Balloon 404 may be configured to switch between the delivery configuration and the deployed configuration through inflation by a pressurized fluid through a fluid channel 408.

Intravascular medical device 400 includes the plurality of therapeutic elements 416 arranged around the perimeter defined by balloon 404. In some examples (not shown), a plurality of temperature sensors may be arranged around the perimeter of balloon 404, such that intravascular medical device 400 may sense a temperature of an inner surface of vessel 410, e.g., with which control circuitry 35 (FIG. 1) may use to control operation of cold therapy source 37. The plurality of therapeutic elements 416 may have any suitable arrangement along balloon 404. For example, therapeutic elements 416 can be arranged on balloon 404 such that, when deployed, therapeutic element 416 may have an axial spacing along and a circumferential spacing around the axis.

Each of the plurality of therapeutic elements 416 is configured to deliver cold therapy to a wall of vessel 410 to remove heat from tissues within vessel 410. The plurality of therapeutic elements 416 may include any therapeutic element configured to contact vessel 410 through one or more surfaces and draw heat from the one or more surfaces, such as to another interface or fluid. A variety of therapeutic elements may be used including, but not limited to, thermoelectric elements, conductive elements configured to receive or contact a cooling fluid (e.g., liquid nitrogen), and the like.

In some examples, the plurality of therapeutic elements 416 may be a plurality of thermoelectric elements, such as one or more Peltier devices. Thermoelectric elements may be configured to receive a voltage (e.g., from cold therapy source 37 under the control of control circuitry 35 (FIG. 1)) and transfer heat from a surface of the thermoelectric element (e.g., cold junction) to another surface (e.g., hot junction) within intravascular medical device 400. As one example, the plurality of thermoelectric elements may include one or more Peltier devices that include a distal cold junction at a surface of the thermoelectric element, a proximal hot junction, and one or more channels within intravascular medical device 400 through which a cooling liquid flows to remove heat from the proximal hot junction, thereby reducing over-heating of the hot junction of the plurality of thermoelectric elements. An amount and distribution of cold therapy may be controlled by controlling a voltage supplied to particular therapeutic elements of the plurality of therapeutic elements 416. In some examples, control circuitry 35 is configured to apply a voltage to all the therapeutic elements 416 simultaneously. In other examples, control circuitry 35 can select a subset of therapeutic elements 416 (less than all the available therapeutic elements 416) to deliver the cold therapy. For example, control circuitry 35 can control therapy source 37 to apply a particular voltage to particular electrical conductors 418 to deliver an amount (e.g., a cooling load) of cold therapy from one or more therapeutic elements 416 at particular axial and/or circumferential positions.

In examples in which the plurality of therapeutic elements 416 are electrically-modulated therapeutic elements, intravascular medical device 400 includes at least one electrical conductor 418 within elongated body 402 and balloon 404 for electrically coupling the plurality of therapeutic elements 416 to an electrical source, such as an electrical source of generator 30 of FIG. 1. In some examples, each therapeutic element 416 may be coupled to a respective electrical conductor 418; however, in other examples, two or more therapeutic elements 416 may be electrically coupled to the same electrical conductor 418, such as shown in FIG. 4A. Thus, intravascular medical device 400 is configured to receive one or more electrical signals from generator 30 and deliver cold therapy to the treatment site within vessel 410.

In some examples, the pressurized fluid delivered to inflate balloon 404 may include a thermal medium configured to remove additional heat from vessel 410, such as described in FIGS. 3A-3C. For example, a thermal medium used to expand balloon 404 may remove heat from vessel 410 in a first stage of cooling to apply cold therapy to large portion of vessel 410, while a plurality of therapeutic elements 416 may remove heat from vessel in a second stage of cooling to apply cold therapy to smaller portions of vessel 410, such that a temperature of the portions of vessel 410 in contact with the plurality of therapeutic elements may be lower than a temperature of the portions of vessel 410 that are in contact with an outer surface of balloon 404. In some examples, a heat flux into the thermal medium may be less than a heat flux into the plurality of therapeutic elements 416.

In some examples, intravascular medical devices described herein may include a helical or a spiral structure as an expansion device for contacting a plurality of therapeutic elements against a wall of a vessel. FIG. 4B is an expanded side view conceptual illustration of a distal portion of an example intravascular medical device that removes heat using thermoelectric elements on a spiral expansion device 424, in accordance with some examples of the present disclosure. Intravascular medical device 420 include a plurality of therapeutic elements 436 electrically coupled to one or more electrical conductors 438, which may be similar to the plurality of therapeutic element 416 and electrical conductors 418 of FIG. 4A above.

Intravascular medical device 420 includes spiral expansion device 424 coupled to an elongated body 422, such as elongated member 16 of intravascular medical device 12 of FIG. 1. Expansion device 424 defines a longitudinal axis and is configured to be positioned within vessel 410 of a patient. Expansion device 424 may be configured to switch between a delivery configuration, in which the expansion device 424 is relatively straight, to a deployed configuration as shown, in which expansion device 424 defines a spiral (or helix). In the deployed configuration, expansion device 424 defines a perimeter that can extend along an inner surface of vessel 410, such that a plurality of therapeutic elements 436 at an outer surface of expansion device 424 may contact the inner surface of vessel 410. Expansion device 424 may be configured to switch between the delivery configuration and the deployed configuration using any of a number of mechanisms, such as actuation of a shape memory member within expansion device 424, actuation of a pull or push wire within expansion device 424, use of a delivery catheter that constrains expansion device 424 to a lower profile configuration for delivery, or the like or combination thereof.

Although FIG. 4B illustrates the spiral defined by expansion device 424 extending to one side of elongated body 422, in other examples, elongated body 422 can be centered or more centered than that shown in FIG. 4B with a center of the spiral or helix defined by expansion device 424.

In some examples, intravascular medical devices described herein may include a net or cage as an expansion device for contacting a plurality of therapeutic elements against a wall of a vessel. FIG. 4C is an expanded side view conceptual illustration of a distal portion of an example intravascular medical device that is configured to remove heat using thermoelectric elements on a net structure, in accordance with some examples of the present disclosure. Intravascular medical device 420 include a plurality of therapeutic elements 456 electrically coupled to one or more electrical conductors 458, which may be similar to the plurality of therapeutic element 416 and electrical conductors 418 of FIG. 4A above.

Intravascular medical device 440 includes a mesh expansion device 444 coupled to elongated member 442, defining a longitudinal axis, and configured to be positioned within vessel 410. In the example of FIG. 4C, expansion device 444 is an expandable mesh structure configured to expand to contact an inner surface of vessel 410. Other designs of expansion device 444 may include, but are not limited to, a hoop, a cage, a basket, and the like. In some examples, expansion device 444 may be self-expanding, while in other examples, expansion device 444 may be expanded by an actuator, such as a push or pull wire, or via withdrawal of a delivery catheter that constrains expansion device 444 to a lower profile configuration for delivery, or the like or combination thereof.

Intravascular medical devices of cold therapy systems described herein can be configured to remove heat from a vessel using a variety of methods and/or mechanisms, including any method or mechanism capable of removing heat from within a small area (e.g., cross-sectional area of a vessel) and reducing a temperature of smooth muscle cells in the wall of the vessel below a temperature at which ablation of the smooth muscle cells occurs.

Figure 5A:
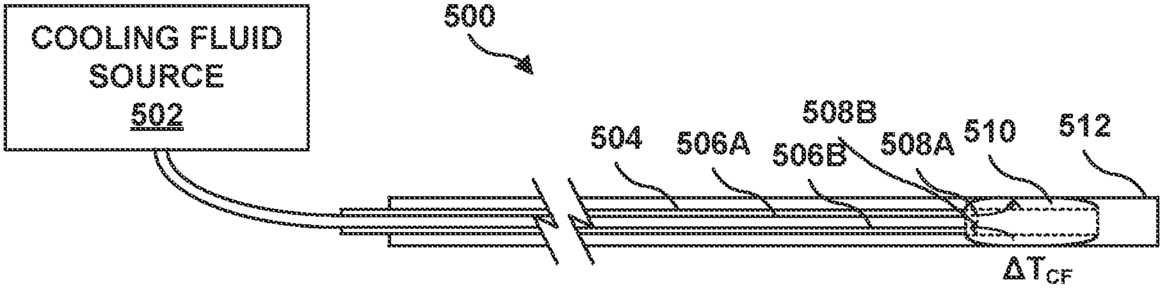
FIG. 5A is an expanded side view conceptual illustration of a distal portion of an example intravascular medical device configured to remove heat from a vessel wall using a cooling fluid in a balloon, in accordance with some examples of the present disclosure.
Figure 5B:
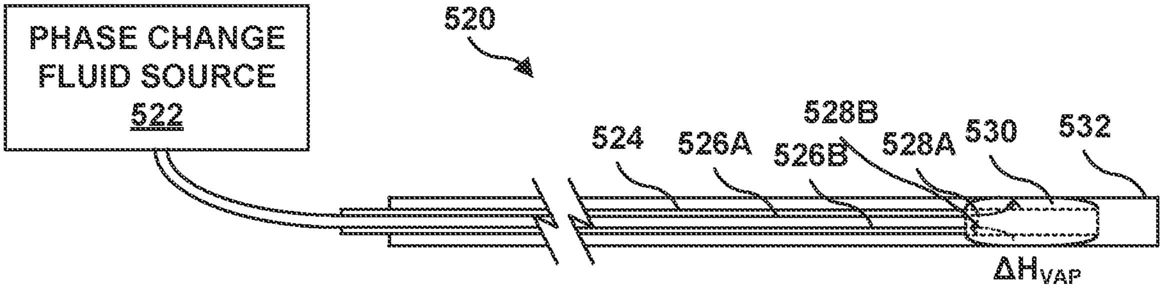
FIG. 5B is an expanded side view conceptual illustration of a distal portion of an example intravascular medical device configured to remove heat from a vessel wall using a phase change fluid in a balloon, in accordance with some examples of the present disclosure.
Figure 5C:
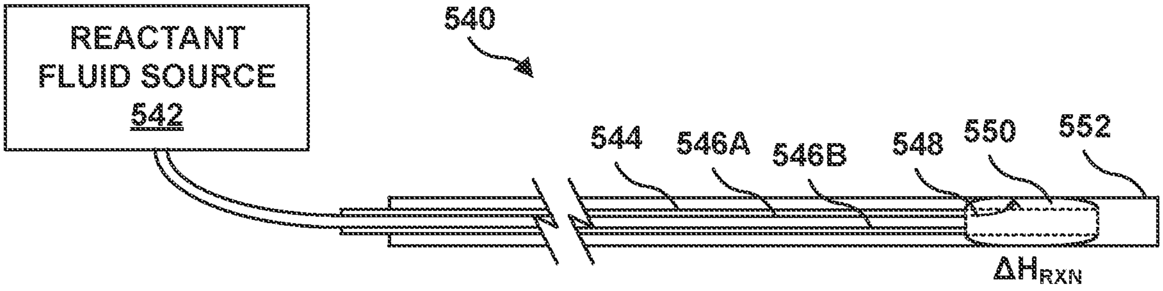
FIG. 5C is an expanded side view conceptual illustration of a distal portion of an example intravascular medical device configured to remove heat from a vessel wall using a chemical reaction in a balloon, in accordance with some examples of the present disclosure.

In some examples, a cold therapy system may apply cold therapy using a cooling fluid. FIGS. 5A-5C illustrate examples of intravascular device 12 of FIG. 1. FIG. 5A is an expanded side view conceptual illustration of a distal portion of an example intravascular medical device 500 that is configured to remove heat using a one-phase cooling fluid (e.g., >0.9 quality) in a balloon 510, in accordance with some examples of the present disclosure. Balloon 510 is an example of cold therapy assembly 14 of FIG. 1. Intravascular medical device 500 includes balloon 510 coupled to an elongated member 504, a fluid inlet 508A configured to discharge cooling fluid into balloon 510, and a fluid outlet configured to discharge cooling fluid from balloon 510. Intravascular medical device 500 is fluidically coupled to cooling fluid source 502 and configured to receive cooling fluid from cooling fluid source 502 via fluid inlet 508A and discharge cooling fluid to cooling fluid source 502 via fluid outlet 508B.

Balloon 510 is configured to receive and discharge a cooling fluid as a thermal medium to absorb heat from the wall of a vessel 512 and expand in response to a positive pressure differential of the cooling fluid across balloon 510. For example, fluid inlet 508A may receive cooling fluid at a first temperature and a first pressure and fluid outlet 508B may discharge cooling fluid at a second, higher temperature and a second, lower pressure. A variety of cooling fluids may be used including, but not limited to, refrigerant, liquid nitrogen, liquid carbon dioxide, water, saline, or the like, or any combination thereof.

Cooling fluid source 502 to control a cooling load of the cooling fluid. For example, cooling fluid source 502 can include therapy generator 30 of FIG. 1 and control circuitry 35 can perform one or more of the functions attributed to cooling fluid source 502 herein. The cooling load may be a function of a rate of cooling fluid entering balloon 510, a temperature of cooling fluid entering balloon 510, and an amount of time for which cooling fluid enters balloon 510. In some examples, to control the cooling load of the cooling fluid, cooling fluid source 502 is configured to control at least one of a flow rate of the cooling fluid to balloon 510 or a temperature of the cooling fluid. For example, cooling fluid source 502 may include a pump or other fluid displacement device configured to deliver pressurized cooling fluid to balloon 510 at a particular pressure or flow rate and/or a heat exchanger or other temperature control device configured to control a temperature of the cooling fluid delivered to balloon 510. The cooling fluid is conditioned (e.g., pumped at a particular rate or to a particular pressure and/or cooled to a particular temperature) to absorb heat from the wall of a vessel 512 and maintain a temperature gradient TCF between a temperature of the cooling fluid and a temperature of the wall of vessel 512. For example, cooling fluid source 502 may maintain a pressure within balloon 510 sufficient to ensure contact between an outer surface of balloon 510 and an inner surface of vessel 512, while also maintaining a sufficiently high flow rate and/or low temperature to provide a particular cooling load to balloon 510.

In some examples, a cold therapy system may apply cold therapy using a phase change fluid. FIG. 5B is an expanded side view conceptual illustration of a distal portion of an example intravascular medical device 520 that removes heat using a phase change fluid in a balloon 530, in accordance with some examples of the present disclosure. Intravascular medical device 520 is an example of intravascular medical device 12 of FIG. 1, and balloon 510 is an example of cold therapy assembly 14 of FIG. 1. Intravascular medical device 520 includes balloon 530 coupled to an elongated member 524, a fluid inlet 528A configured to discharge liquid phase change fluid into balloon 530, and a fluid outlet configured to discharge gaseous phase change fluid from balloon 530. Intravascular medical device 520 is fluidically coupled to phase change fluid source 522 and configured to receive phase change fluid from phase change fluid source 522 via fluid inlet 528A and discharge phase change fluid to phase change fluid source 522 via fluid outlet 528B.

Balloon 530 is configured to receive and discharge a phase change fluid as a thermal medium to absorb heat from the wall of a vessel 532 and expand in response to a positive pressure differential of the phase change fluid. For example, fluid inlet 528A may receive a phase change fluid at a first temperature, a first pressure, a first density, and a substantially liquid state (e.g., >0.9 quality) and fluid outlet 528B may discharge the phase change fluid at a second, higher temperature, a second, lower pressure, a second, lower density, and a partially (e.g., <0.5 quality) or substantially gaseous state (e.g., <0.2 quality). A variety of phase change fluids may be used including, but not limited to, liquid nitrogen, liquid carbon dioxide, refrigerant, and the like. In some examples, the phase change fluid has a boiling point at a working pressure (e.g., a pressure conducive with operating constraints of intravascular medical device 520) that is within a target therapy range for ablating smooth muscle cells of vessel 532 while leaving structural proteins intact. In some examples, the phase change fluid has a boiling point of less than about 0° C. at a pressure less than about 1.7 MPa (about 250 psi).

Phase change fluid source 522 is configured to control a cooling load of the phase change fluid. For example, phase change fluid source 522 can include therapy generator 30 of FIG. 1 and control circuitry 35 can perform one or more of the functions attributed to phase change fluid source 522 herein. The cooling load may be a function of a rate of liquid phase change fluid entering balloon 530, a temperature of liquid phase change fluid entering balloon 530, a boiling point of the phase change fluid entering balloon, a pressure of liquid phase change fluid entering balloon 530, a pressure of mixed or gaseous phase change fluid within balloon 530, and an amount of time for which the phase change fluid enters balloon 530. In some examples, to control the cooling load of the phase change fluid, phase change fluid source 522 is configured to control a flow rate of the phase change fluid into balloon 530, a pressure of phase change fluid entering balloon 530, and/or a temperature of phase change fluid entering balloon 530. The phase change fluid is conditioned (e.g., pumped at a particular rate or to a particular pressure and/or cooled or condensed to a particular temperature) to absorb heat from the wall of a vessel 532 and maintain a low temperature within balloon 530 by evaporating a phase change fluid according to a heat of vaporization $\Delta H_{VAP}$. For example, phase change fluid source 522 may maintain a pressure or quality within balloon 530 sufficient to ensure contact between an outer surface of balloon 530 and an inner surface of vessel 532, while also maintaining a sufficiently high flow rate, high pressure, and/or low temperature of the phase change fluid to provide a particular cooling load to balloon 530.

In some examples, rather than using a phase change fluid, cold therapy systems may include a compressible fluid configured to change pressure and, corresponding, reduce an enthalpy of the compressible fluid. For example, the compressible fluid may expand and correspondingly drop in temperature to remove heat from a balloon.

In some examples, a cold therapy system may apply cold therapy using an endothermic chemical process, such as an endothermic chemical reaction or decomposition. FIG. 5C is an expanded side view conceptual illustration of a distal portion of an example intravascular medical device 540 that removes heat using a chemical reaction in balloon 550, in accordance with some examples of the present disclosure. Intravascular medical device 540 is an example of intravascular medical device 12 of FIG. 1, and balloon 550 is an example of cold therapy assembly 14 of FIG. 1. Intravascular medical device 540 includes balloon 550 coupled to an elongated member 544 and a fluid inlet 548 configured to discharge a reactant fluid into balloon 550. In some examples, intravascular medical device 540 may include a fluid outlet configured to discharge a reaction product from balloon 550, such as to manage a pressure within balloon 550. Intravascular medical device 540 is fluidically coupled to reactant fluid source 542 and configured to receive a reactant fluid from reactant fluid source 542 via fluid inlet 548 and, optionally, discharge reactant products to reactant fluid source 542 (or another system) via a fluid outlet.

Balloon 550 is configured to contain one or more reactant and/or product fluids as a thermal medium to absorb heat from the wall of a vessel 512 and expand in response to a positive pressure differential of the reactant fluid and/or reaction products. For example, an endothermic reaction may include any reaction between one or more reactants and one or more products that removes heat from the surrounds and transfers the heat into the system. Balloon 550 is configured to receive at least one reactant as a reactant fluid. The at least one reactant may absorb heat from balloon 550 and react with another reactant, such as a reactant introduced through fluid inlet 548 or already present within balloon 550, to produce one or more products, at least one of which may be a gaseous product. The gaseous product may expand balloon 550 to contact vessel 552, such that heat absorbed by the reactants and/or products may be removed from vessel 552 via balloon 550. A variety of reactants may be used including, but not limited to, [example reactants], and the like.

Reactant fluid source 542 is configured to control a cooling load of the endothermic chemical reaction within balloon 550. For example, reactant fluid source 542 can include therapy generator 30 of FIG. 1 and control circuitry 35 can perform one or more of the functions attributed to reactant fluid source 542 herein. The cooling load may be a function of a composition of one or more reactants, a rate of reactant fluid entering balloon 550, a temperature of reactant fluid entering balloon 550, a pressure of reactant fluid entering balloon 550, an extent of the endothermic chemical reaction within balloon 550, a concentration of the one or more reactants and/or one or more products, and an amount of time for which the phase change fluid enters balloon 550. In some examples, to control the cooling load of the endothermic chemical reaction within balloon 550, reactant fluid source 542 is configured to control a flow rate of at least one reactant of the endothermic chemical reaction to the cavity of balloon 550. Reactant fluid source 542 conditions the reactant fluid (e.g., pumps the fluid at a particular rate or in a particular concentration) to absorb heat from the wall of a vessel 552 as the endothermic reaction progresses and maintain a low temperature within balloon 550 by remove heat from balloon 550 according to a heat of reaction $\Delta H_{RXN}$. For example, reactant fluid source 542 may maintain a rate of reaction that produces a pressure within balloon 550 sufficient to ensure contact between an outer surface of balloon 550 and an inner surface of vessel 552, while also maintaining a rate of reaction within balloon 550 to provide a particular cooling load to balloon 550.

Figure 5D:
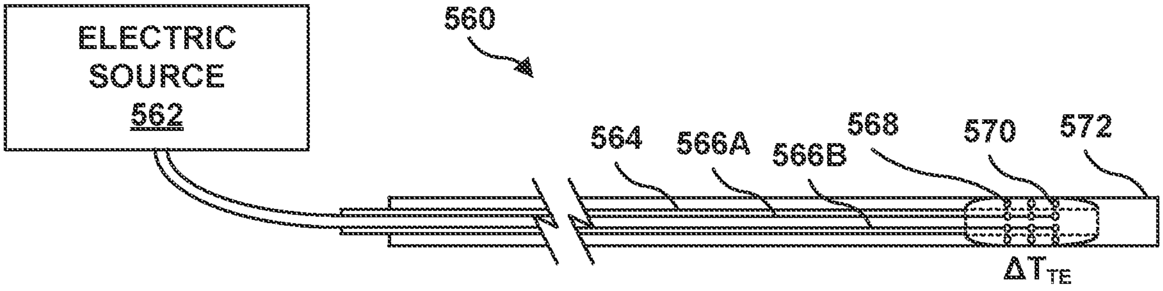
FIG. 5D is an expanded side view conceptual illustration of a distal portion of an example intravascular medical device configured to remove heat from a vessel wall using therapeutic elements on a balloon, in accordance with some examples of the present disclosure.

In some examples, a cold therapy system may apply cold therapy using one or more therapeutic elements. FIG. 5D is an expanded side view conceptual illustration of a distal portion of an example intravascular medical device 560 that removes heat using thermoelectric elements 568 on a balloon 570, in accordance with some examples of the present disclosure. Intravascular medical device 540 is an example of intravascular medical device 12 of FIG. 1, and thermoelectric elements 568 and balloon 550 are an example of cold therapy assembly 14 of FIG. 1. Intravascular medical device 560 includes balloon 570 coupled to an elongated member 564, a first electrical conductor 566A configured to delivery current to a first set of thermoelectric elements 568 and a second electrical conductor 566B configured to deliver current to a second set of thermoelectric elements 568, and one or more fluid inlets/outlets (not shown) configured to deliver and discharge a pressurized fluid from balloon 570. Balloon 570 is configured to receive and discharge a pressurized fluid and expand in response to a positive pressure differential of the pressurized fluid across balloon 570.

In the example of FIG. 5D, the plurality of therapeutic elements includes a plurality of thermoelectric elements 568 configured to change temperature in response to an applied voltage. Intravascular medical device 560 is electrically coupled to electric source 562 and configured to receive electrical current from electric source 562 via electrical conductors 566A and 566B. For example, under the control of control circuitry, electrical conductor 566A may receive an electrical current at a first voltage and electrical conductor 566B may receive an electrical current at a second voltage.

Electric source 562 is configured to control the electrical current to the plurality of thermoelectric elements 568. For example, electric source 562 can include therapy generator 30 of FIG. 1 and control circuitry 35 can perform one or more of the functions attributed to electric source 562 herein. For example, electric source 562 may be configured to control a voltage of the electrical current applied to the plurality of thermoelectric elements 568. Electric source 562 conditions the electrical current (e.g., delivers the current at a particular voltage) to control a temperature of the plurality of thermoelectric elements 568 to cause the plurality of thermoelectric elements 568 to absorb heat from the wall of a vessel 572 and maintain a temperature gradient $\Delta T_{TE}$ between a temperature of the plurality of thermoelectric elements 568 and a temperature of the wall of vessel 512. For example, a pressurized fluid source (not shown) may maintain a pressure within balloon 570 sufficient to ensure contact between the plurality of thermoelectric elements 568 and an inner surface of vessel 572, while electric source 562 may maintain an applied voltage to the plurality of thermoelectric elements 568 to provide a particular cooling load to vessel 572. In some examples, electric source 562 is configured to apply a different voltage to particular thermoelectric elements of the plurality of thermoelectric elements 568.

For example, electric source 562 may be configured to deliver electrical current at a first voltage to the first set of thermoelectric elements coupled to electrical conductor 566A corresponding to a first temperature of the first set of thermoelectric elements and deliver electrical current at a second voltage to the second set of thermoelectric elements coupled to electrical conductor 566B corresponding to a second, lower temperature of the second set of thermoelectric elements.

Figure 6:
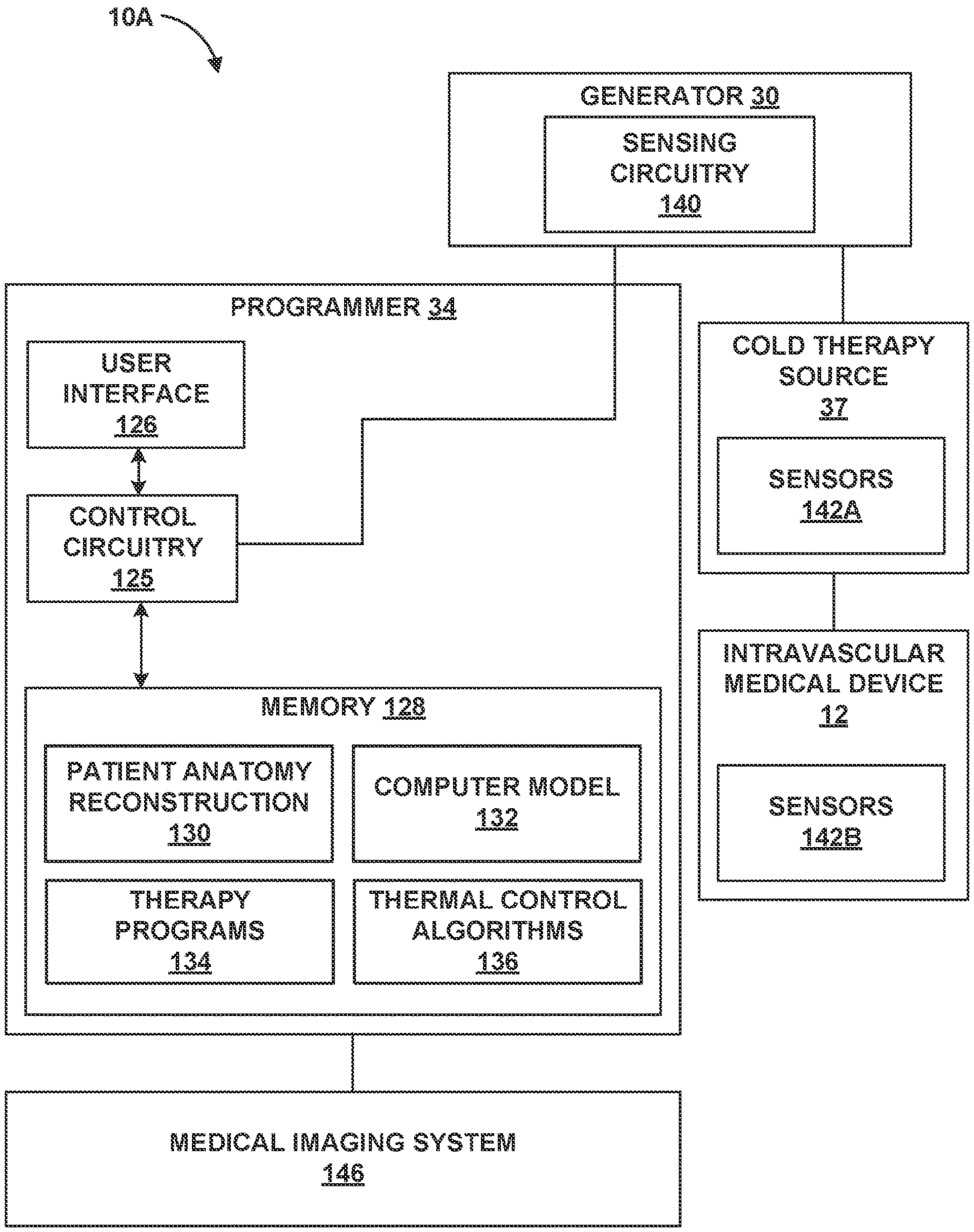
FIG. 6 is a schematic and conceptual illustration of an example programmer coupled to an imaging system and an example intravascular medical device, in accordance with some examples of the present disclosure.

FIG. 6 is a schematic and conceptual illustration of an example programmer 34 coupled to a medical imaging system 146 and an example intravascular medical device 12, in accordance with some examples of the present disclosure. In some examples, system 10A is similar to system 10 described with reference to FIG. 1. Instead of, or in addition to, control circuitry 35 and memory 38 in cold therapy generator 30, system 10A may include programmer 34 including a control circuitry 125, a user interface 126, and a memory 128. In some examples, control circuitry 35 and memory 38 in cold therapy generator 30 may perform functions described with reference to control circuitry 125 and memory 128.

Memory 128 includes computer-readable instructions that, when executed by control circuitry 125, causes programmer 34 to perform various functions. Control circuitry 125 may include any one or more microprocessors, controllers, DSPs, ASICs, FPGAs, or equivalent discrete or integrated digital or analog logic circuitry, and the functions attributed to control circuitry 125 herein may be embodied as software, firmware, hardware or any combination thereof. Memory 128 may include any volatile, non-volatile, magnetic, optical, or electrical media, such as RAM, ROM, NVRAM, EEPROM, flash memory, or any other digital media. Memory 128 may store any suitable information, including patient identification information, and information for generating one or more cold therapy programs with which generator 30 generates and delivers cold therapy to a patient to expand a constricted vessel. For example, memory 128 may store one or more of patient anatomy reconstruction 130, computer model 132, cold therapy programs 134, thermal control algorithms 136, and operating instructions in separate memories within memory 128 or separate areas within memory 128. Memory 128 may also store operating instructions with which control circuitry 125 controls the operation of programmer 34, and may include instructions for determining placement and orientation of cold therapy assembly 14 along the vessel.

In examples in which system 10A includes programmer 34, generator 30 can be configured to receive one or more cold therapy parameter values with which generator 30 generates and delivers vascular therapy via programmer 34. In some examples, generator 30 or programmer 34 may include one or more evaluation or feedback modules to provide feedback to the clinician before, during, and/or after vascular therapy.

In some examples, functions described elsewhere with reference to programmer 34 may be performed by generator 30, and system 10A may not include a separate programmer. Thus, system 10A may include a memory (for example, in generator 30 or programmer 34) configured to store one or more tissue characteristics of tissue proximate a vessel of a patient, and control circuitry coupled to the memory. The control circuitry is configured to determine one or more tissue characteristics of tissue proximate a vessel and generate, based on the one or more tissue characteristics, an estimated volume of influence (e.g., temperatures below an ablation temperature of the tissue) of vascular therapy delivered by intravascular medical device 12 disposed within the vessel. The control circuitry is configured to generate a GUI that provides information to a clinician to help visualize vascular therapy, and determine the effects of different therapy delivery parameters. In some examples, the GUI includes a graphical representation of the tissue proximate the vessel and a graphical representation of the estimated volume of influence.

In some examples, the functioning of intravascular medical device 12 and generator 30 may be controlled by programmer 34 or other control circuitry described herein based on an estimated cooling load of cold therapy for modifying a structure of a vessel by substantially ablating smooth muscle cells of a vessel while substantially leaving structural proteins intact. For example, programmer 34 may determine one or more therapy parameters for a cold therapy program for achieving predetermined levels of ablation of smooth muscle cells in a target region of a vessel of a patient. The clinician, generator 30, or programmer 34, optionally may choose which cold therapy elements are used for cold therapy delivery in order to form customized treatment regions within the vessel having a variety of predetermined shapes or patterns. The selection of the particular cold therapy elements with which a cold therapy application is delivered to tissue is one example of a therapy delivery parameter value that programmer 34 can determine using the computer modeling techniques described herein.

In some examples, programmer 34 may generate or use therapy programs 134 for determining therapy parameters. For example, each therapy program 134 defines a particular program of cold therapy in terms of respective values for cold therapy parameters, such as measured parameters of cold therapy assembly 14, such as temperature of one or more surfaces of cold therapy assembly 14; control parameters of a fluid delivered to cold therapy assembly 14, such as a temperature of the fluid, a pressure of the fluid, or a flow rate of the fluid; control parameters of one or more therapeutic elements of cold therapy assembly 14, such as a voltage delivered to cold therapy assembly 14 or one or more therapeutic elements, current or voltage amplitude, and/or frequency; or any combination thereof.

Generator 30 is configured to receive one or more cold therapy programs 134 from programmer 34, and, under the control of control circuitry 35, apply the cold therapy parameter values specified by the received one or more cold therapy programs 134, such as temperature of one or more surfaces of cold therapy assembly 14, temperature of one or more therapeutic elements of cold therapy assembly 14, pressure of cold therapy assembly 14, temperature of fluid, flow rate of fluid, and other controllable parameters that may affect a cooling load delivered by cold therapy assembly 14, or combination of parameters. For example, generator 30 may control cold therapy source 37 (FIG. 1) to generate a distribution of cold therapy according to a particular therapy program, and deliver the cold therapy via intravascular medical device 12.

Cold therapy source 37 may be configured to deliver a particular distribution of cold therapy. For example, in examples in which cold therapy source 37 includes electrical current or other electrical energy delivery circuitry, cold therapy source 37 may be electrically coupled to the one or more conductors of intravascular medical device 12 using any suitable technique. For example, generator 30 may include switching circuitry configured to switch the electrical current generated by cold therapy source 37 across different therapeutic elements or cold therapy source 37 may include multiple energy sources to deliver energy to one or more therapeutic elements at one time.

In some examples, generator 30 includes sensing circuitry 140 coupled to intravascular medical device 12 and/or cold therapy source 37, for example, to receive electrical measurements, feedback, or signals, for example, temperature, which control circuitry 35 of generator 30 may automatically control the delivery of cold therapy via intravascular medical device 12, in a closed-loop or pseudo closed-loop manner. In some examples, sensing circuitry 140 may be communicatively coupled to one or more sensors 142A in cold therapy source 37 and/or one or more sensors 142B in intravascular medical device 12.

A user, either a clinician or patient, may interact with control circuitry 125 through user interface 126. User interface 126 may include a display, such as a liquid crystal display (LCD), light-emitting diode (LED) display, or other screen, to present information related to stimulation therapy, and buttons or a pad to provide input to programmer 34. In examples in which user interface 126 requires a 3D environment, the user interface may support 3D environments such as a holographic display, a stereoscopic display, an autostereoscopic display, a head-mounted 3D display, or any other display that is capable of presenting a 3D image to the user. Buttons of user interface 126 may include an on/off switch, plus and minus buttons to zoom in or out or navigate through options, a select button to pick or store an input, and pointing device, e.g., a mouse, trackball, or stylus. Other input devices may be a wheel to scroll through options or a touch pad to move a pointing device on the display. In some examples, the display may be a touch screen that enables the user to select options directly from the display screen.

In some examples, programmer 34 includes a telemetry module configured to support wired or wireless communication between programmer 34 and generator 30 or another computing device under the control of control circuitry 125. A clinician or another user may interact with programmer 34 to generate and/or select therapy programs 134 for delivery via intravascular medical device 12. In some examples, programmer 34 may allow a clinician to define target regions, such as cold therapy regions 230 of FIG. 2C, and generate appropriate cold therapy delivery parameter values to achieve the desired cold therapy regions 230. Programmer 34 may be used to present anatomical regions to the clinician via user interface 126, select therapy programs 134, generate new therapy programs 134 by manipulating a computer model 132 or estimated cold therapy regions 230 presented on a GUI on user interface 126, and communicate the selected therapy programs 134 to the generator 30.

Programmer 34 may include a power source for delivering operating power to the components of programmer 34. The power source may include at least one battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries (e.g., nickel cadmium or lithium ion batteries) may be used. In addition, programmer 34 may be directly coupled to an alternating current source, such would be the case with some computing devices, such as personal computers. The power source may include circuitry to monitor power remaining within a battery. In this manner, user interface 126 may provide a current battery level indicator or low battery level indicator when the battery needs to be replaced or recharged. In some cases, the power source may be capable of estimating the remaining time of operation using the current battery.

In some examples, programmer 34 may be communicatively coupled to medical imaging system 146, or may otherwise receive one or more medical images of a patient from medical imaging system 146. Medical imaging system 146 may be configured to generate a medical image of a region of a patient that includes a target vessel (e.g., intended to be modified). One or more medical images generated by medical imaging system 146 may be stored by programmer 34 in memory 128, or otherwise used by control circuitry 125, to generate patient anatomy digital reconstruction 130. The medical image can be any medical image that provides sufficient resolution for identifying the tissue regions to avoid (for example, particular muscles, lymph nodes, other blood vessels veins/arteries, or other anatomical features or tissue).

In some cases, memory 128 of programmer 34 or another device (e.g., a remote device) may store a plurality of medical images of a patient, which can be, for example, a plurality of medical images of the same or nearly the same region of the patient. In some cases, if there has been a relatively large gap of time between cold therapy sessions (e.g., on the order of weeks, months, or even years), a clinician may elect to use medical imaging system 146 to generate one or more updated medical images of the patient or otherwise obtain updated medical images of the patient, and update the one or more therapy programs used by generator 30 based on the one or more updated medical images. In some examples, the plurality of medical images may include any suitable available medical images of the patient region, for example, images obtained of the patient region obtained for a therapy other than cold therapy. There may be changes to a particular patient's anatomy and/or tissue characteristics over time, such as due to weight gain, weight loss, or the like.

In some examples, medical imaging system 146 includes at least one of a fluoroscopy system, a computer aided tomography (CAT) scan system, a magnetic resonance imaging (MRI) system, a positron emission tomography (PET) scan system, an electrical impedance tomography (EIT) system, an ultrasound system, or an optical imaging system. In some examples, control circuitry 125 is configured to develop computer model 132 based on patient anatomy reconstruction 130. In some examples, computer model 132 includes a finite element model. In some examples, digital reconstruction 130 includes a three-dimensional (3D) reconstruction. Processor 125 may use one or both of digital reconstruction 130 or computer model 132 to determine an estimated volume of influence of cold therapy, such as based on an anticipated cooling load for achieving a temperature of smooth muscle cells within a particular therapy range, and determine one or more therapy programs 134 based on the estimated volume of influence, such as therapy programs 134 that include parameters related to achieving a target temperature at a surface of cold therapy assembly 14, a target temperature at an inner surface of the vessel (e.g., based on data from sensors 142B), and/or a target amount of time for which cold therapy is applied to the vessel. Processor 125 may further also be used to deliver and monitor delivery of cold therapy by generator 30 based on therapy programs 134, as described with reference to FIGS. 7A-7C below.

Figure 7A:
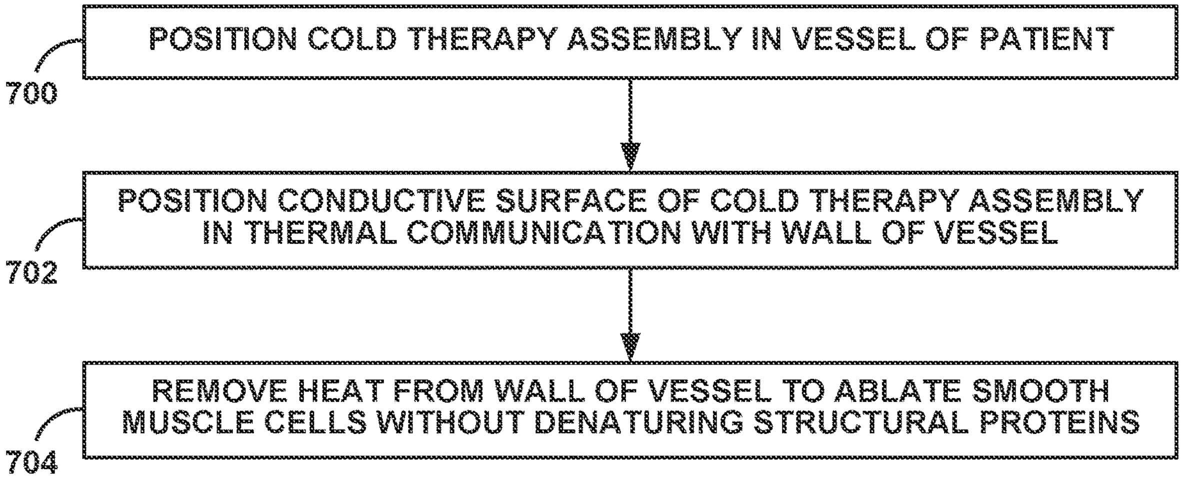
FIG. 7A is a flowchart of an example method for applying a cold therapy to a wall of a vessel, in accordance with some examples of the present disclosure.

FIG. 7A is a flowchart of an example method for applying a cold therapy to a wall of a vessel, in accordance with some examples of the present disclosure. FIG. 7A will be described with respect to system 10 of FIG. 1 and artery 200 of FIGS. 2A-2E, but applies to other examples systems, devices, and target hollow anatomical structures of a patient. The method of FIG. 7A includes positioning cold therapy assembly 14 in a vessel of a patient (700). For example, a clinician may manipulate hub 18 or other handle and advance a distal end of intravascular medical device 12 to a target treatment site of a wall of the vessel of the patient, such that cold therapy assembly 14 is positioned proximate the target treatment site. With the aid a medical imaging device, the clinician may confirm a position of cold therapy assembly 14 in the vessel. As described in FIG. 2A, a wall of the vessel includes smooth muscle cells and one or more structural proteins, such as elastin and collagen.

The method of FIG. 7A includes positioning one or more surfaces of cold therapy assembly 14 in thermal communication with the wall of the vessel (702). As described in FIGS. 3A-3C and 4A-4C, cold therapy assembly 14 may include an expansion device configured to expand such that one or more thermal surfaces of cold therapy assembly 14 are in thermal communication with (e.g., contact or are proximate to) the wall of the vessel at the target treatment site. For example, the clinician may operate hub 18 or cold therapy source 37 to deliver a pressurized fluid to the expansion device (e.g., a balloon) to radially expand the expansion device, operate an actuation mechanism to radially expand the expansion device, or the like. In some examples, contacting the wall of the vessel with one or more surface of cold therapy assembly 14 may include expanding the expansion device beyond an initial diameter of the vessel.

The method of FIG. 7A includes removing heat from the wall of the vessel to ablate the smooth muscle cells without denaturing the one or more structural proteins (704). To remove heat from the wall of the vessel, therapy generator 30 may be configured to control a cooling load delivered to cold therapy assembly 14. For example, therapy generator 30 may receive various parameters, such as input by the clinician via secondary input 36, associated with an amount of cold therapy to be delivered to the target treatment site. To ablate the smooth muscle cells without substantially denaturing the one or more structural proteins, the heat is removed from the wall of the vessel to achieve and/or maintain a temperature of the smooth muscle cells associated with ablation of the smooth muscle cells. For example, the temperature of the smooth muscle cells may be maintained within a target temperature range for a target therapy time range that corresponds to the cooling load. The target therapy time range can be, for example, stored in a memory of generator 30 or another device, such as a programmer 34 (FIG. 6). In some examples, the target tissue temperature range is defined by an upper temperature threshold value associated with death of the smooth muscle cells and a lower temperature threshold value associated with denaturing of the one or more structural proteins. In some examples, the upper temperature threshold value is less than about 0° C.

Figure 7B:
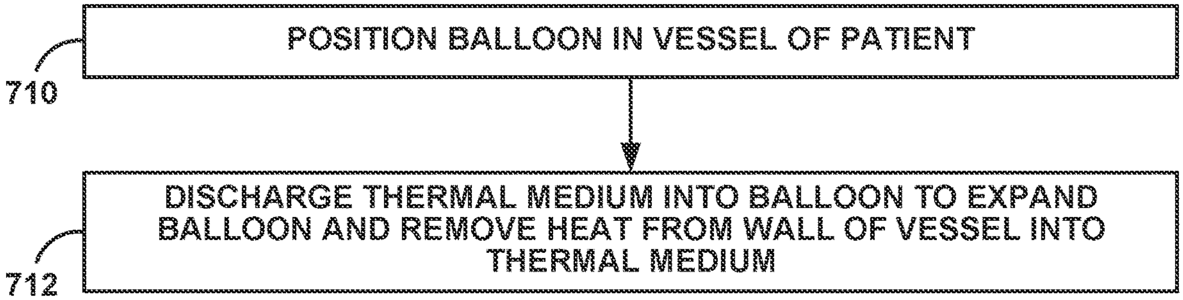
FIG. 7B is a flowchart of an example method for applying a cold therapy to a wall of a vessel using a thermal medium within a balloon, in accordance with some examples of the present disclosure.

In some examples, a cold therapy assembly includes a balloon including a cavity configured to contain a thermal medium, in which removing the heat from the wall of the vessel includes transmitting the heat from the wall of the vessel to the thermal medium. FIG. 7B is a flowchart of an example method for applying a cold therapy to a wall of a vessel using a thermal medium within a balloon, in accordance with some examples of the present disclosure. The method of FIG. 7B will be described with respect to FIGS. 3A-3C and 5A-5C, but can be used with other devices and systems described herein. The method of FIG. 7B include positioning a balloon, such as balloon 510, 530, or 550 of FIGS. 5A-5C, in a respective vessel 512, 532, or 552 of a patient, such as described in step 700 of FIG. 7A above (710). The method of FIG. 7B includes discharging a thermal medium into a cavity of balloons 510, 530, or 550 to expand the respective balloon and remove heat from the wall of a vessel 512, 532, or 552 into the thermal medium (712). For example, a clinician may interact with user interface 126 of programmer 34 or of therapy generator 30 or another device, and cause the fluid source 502, 522, or 542 to deliver the thermal medium to the cavity of the respective balloon.

In examples in which the thermal medium includes a cooling fluid, such as described in FIG. 5A, to expand balloon 510 and remove the heat from the wall of vessel 512, the method includes controlling, by control circuitry, a cooling load delivered by the cooling fluid. For example, control circuitry of cooling fluid source 502 (an example of therapy generator 30) may control a cooling load delivered to balloon 510, such as based on parameters received by the clinician or determined by generator 30 or programmer 34 of FIG. 1 or 6. In some examples, to control the cooling load of the cooling fluid, the method may include controlling, by control circuitry, at least one of a flow rate of the cooling fluid to balloon 510 or a temperature of the cooling fluid. For example, control circuitry of cooling fluid source 502 may control a flow rate of the cooling fluid to balloon 510 or a temperature of the cooling fluid delivered to balloon 510, such that smooth muscle cells at the target treatment site of vessel 512 may be substantially ablated while leaving structural proteins intact.

In examples in which the thermal medium includes a phase change fluid, such as described in FIG. 5B, to expand balloon 530 and remove the heat from the wall of vessel 532, the method includes controlling, by control circuitry, a cooling load of the phase change fluid. For example, control circuitry of phase change fluid source 522 (an example of therapy generator 30) may control a cooling load delivered to balloon 530, such as based on parameters received by the clinician or determined by generator 30 or programmer 34 of FIG. 1 or 6. In some examples, to control the cooling load of the phase change fluid, the method includes controlling, by control circuitry, a pressure of the phase change fluid. For example, control circuitry of phase change fluid source 522 (an example of therapy generator 30) may control a flow rate of a liquid phase change fluid and a pressure of the liquid phase change fluid to evaporate at least a portion of the liquid phase change fluid, thereby expanding the phase change fluid and removing heat from balloon 530. In some examples, the phase change material has a boiling point less than about 0° C. at a working pressure (e.g., less than about 250 psig) within intravascular medical device 520.

In examples in which the thermal medium includes a reactant and/or product of an endothermic chemical reaction, to remove the heat from the wall of the vessel, the method includes controlling a cooling load of the endothermic chemical reaction. For example, reactant fluid source 542 (an example of therapy generator 30) may control a cooling load delivered to balloon 550, such as based on parameters received by the clinician or determined by generator 30 or programmer 34 of FIG. 1 or 6. In some examples, to control the cooling load of the endothermic chemical reaction, the method includes controlling by at least controlling a flow rate of at least one reactant of the endothermic chemical reaction to the cavity to control a rate of reaction of the endothermic chemical reaction and, correspondingly, a rate of heat removal from balloon 550. For example, control circuitry of reactant fluid source 542 may control a flow rate of a reactant fluid to react with another reactant, such as a reactant delivered by reactant fluid source 542 or present in balloon 550, thereby producing a gaseous product to expand balloon 550 and removing heat from balloon 550 as the reaction progresses.

Figure 7C:
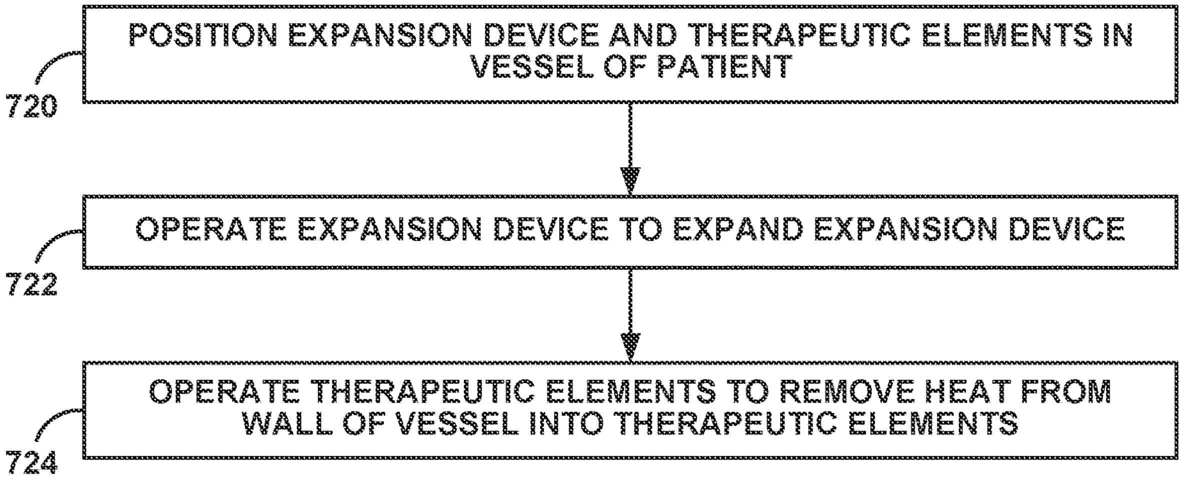
FIG. 7C is a flowchart of an example method for applying a cold therapy to a wall of a vessel using a plurality of therapeutic elements on an expansion device, in accordance with some examples of the present disclosure.

In some examples, a cold therapy assembly includes an expansion device and a plurality of therapeutic elements that include the one or more conductive surfaces, in which removing the heat from the wall of the vessel includes transmitting the heat from the wall of the vessel to the plurality of therapeutic elements. FIG. 7C is a flowchart of an example method for applying a cold therapy to a wall of a vessel using a plurality of therapeutic element on an expansion device, in accordance with some examples of the present disclosure. The method of FIG. 7C will be described with respect to FIGS. 4A-4C and 5D, but can be used with other devices and systems described herein. The method of FIG. 7C include positioning a cold therapy assembly that includes an expansion device and a plurality of therapeutic elements, such as balloon 570 and thermoelectric elements 568 of FIG. 5D, in vessel 572 of a patient, such as described in step 700 of FIG. 7A above (720).

To contact the wall of vessel 572 with one or more conductive surfaces of the plurality of thermoelectric elements 568 or position the plurality of thermoelectric elements 568 proximate to the wall of vessel 572, the method includes operating the expansion device to expand the expansion device and radially extend the one or more conductive surfaces to contact or position proximate to the wall of the vessel (722). In examples in which the expansion device includes a balloon configured to transform from a deflated delivery configuration to an inflated deployed configuration, such as illustrated in FIG. 4A, operating the expansion device may include inflating the balloon, such as balloon 404. In examples in which the expansion device includes a spiral expansion device configured to transform from an elongated delivery configuration to a spiral deployed configuration, such as illustrated in FIG. 4B, operating the expansion device may include actuating spiral expansion device 424 to coil spiral expansion device 424. In examples in which the expansion device includes a mesh expansion device configured to transform from a collapsed delivery configuration to an expanded delivery configuration, such as illustrated in FIG. 4C, operating the expansion device may include actuating the mesh expansion device 444 to expand mesh expansion device 444 or permit mesh expansion device 44 to self-expand.

The method of FIG. 7C includes operating the plurality of therapeutic elements 568 to remove heat from the wall of vessel 572 into the plurality of therapeutic elements 568 (724). In examples in which the plurality of therapeutic elements includes a plurality of thermoelectric elements, such as illustrated in FIG. 5D, the method includes controlling, by control circuitry, the applied voltage to the plurality of thermoelectric elements 568. For example, control circuitry of electric source 562 (an example of therapy generator 30) may control a cooling load delivered to thermoelectric elements 568, such as based on parameters received by the clinician or determined by generator 30 or programmer 34 of FIG. 1 or 6. In some examples, to control the cooling load of the plurality of thermoelectric elements 568, the method may include controlling an applied voltage delivered to the plurality of thermoelectric elements 568 to change a temperature of the plurality of thermoelectric elements. For example, electric source 562 may control a voltage of an electrical current delivered to the plurality of thermoelectric elements 568, such that smooth muscle cells at the target treatment site of vessel 512 may be substantially ablated while leaving structural proteins intact.

Figure 8A:
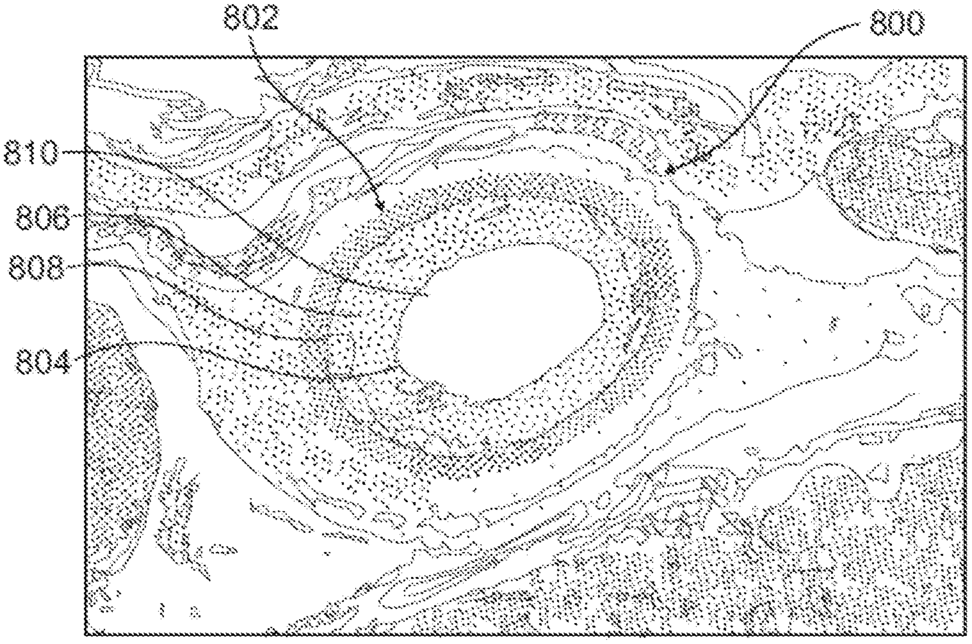
FIG. 8A is a low magnification photomicrograph of a cross-sectional view of an artery prior to cold therapy.
Figure 8B:
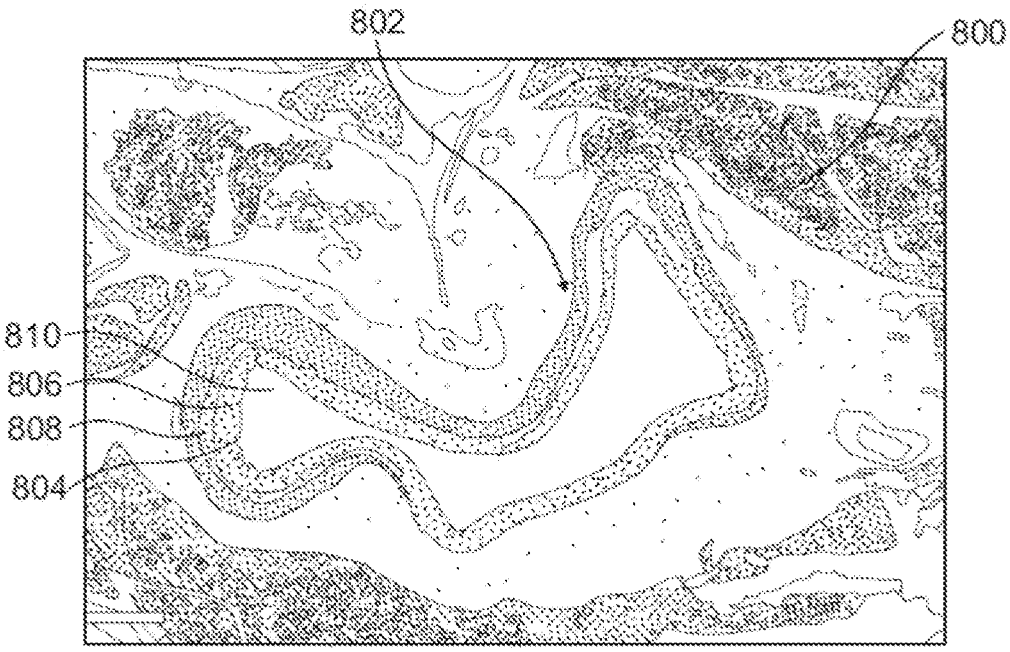
FIG. 8B is a low magnification photomicrograph of a cross-sectional view of an artery after cold therapy, in accordance with some examples of the present disclosure.

Cold therapy systems described herein may be used to modify the wall of a constricted vessel in a patient. FIG. 8A is a low magnification photomicrograph of a cross-sectional view of an artery prior to cold therapy. Wall 802 defines a lumen 810, and includes a tunica intima 804, tunica media 806, and tunica adventitia 808. Prior to cold therapy, wall 802 has a relatively circular shape, due at least in part to a presence of smooth muscle cells in tunica media 806 that support tunic media 806. FIG. 8B is a low magnification photomicrograph of a cross-sectional view of an artery after cold therapy, in accordance with some examples of the present disclosure. Tunica media 806 after cold therapy is substantially thinner than tunica media 806 prior to cold therapy and does not include a smooth muscle component. As a result, wall 802 has an irregular shape that results from an elasticity of intact structural proteins in tunica media 806 and tunica adventitia 808, tissues surrounding artery 800 exerting forces on an outer surface of wall 802, and blood from within lumen 810 exerting forces on an inner surface of wall 802. While lumen 810 after cold therapy may have an irregular shape, a cross-sectional area of lumen 810 after cold therapy may be greater than a cross-sectional area of lumen 810 prior to cold therapy.

Figure 8C:
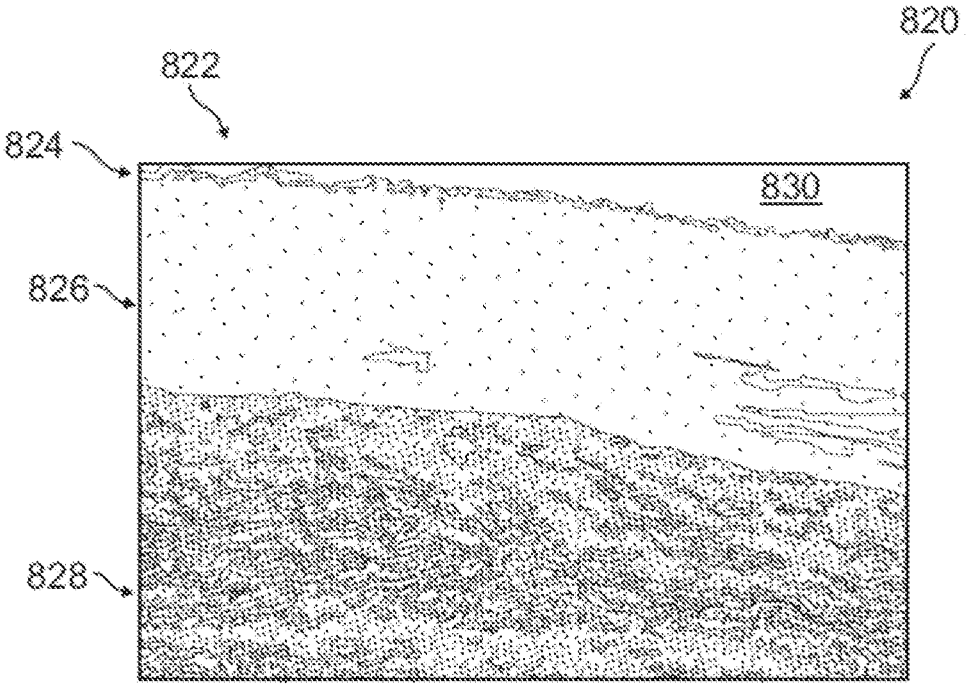
FIG. 8C is a high magnification photomicrograph of a cross-sectional view of an artery prior to cold therapy.
Figure 8D:
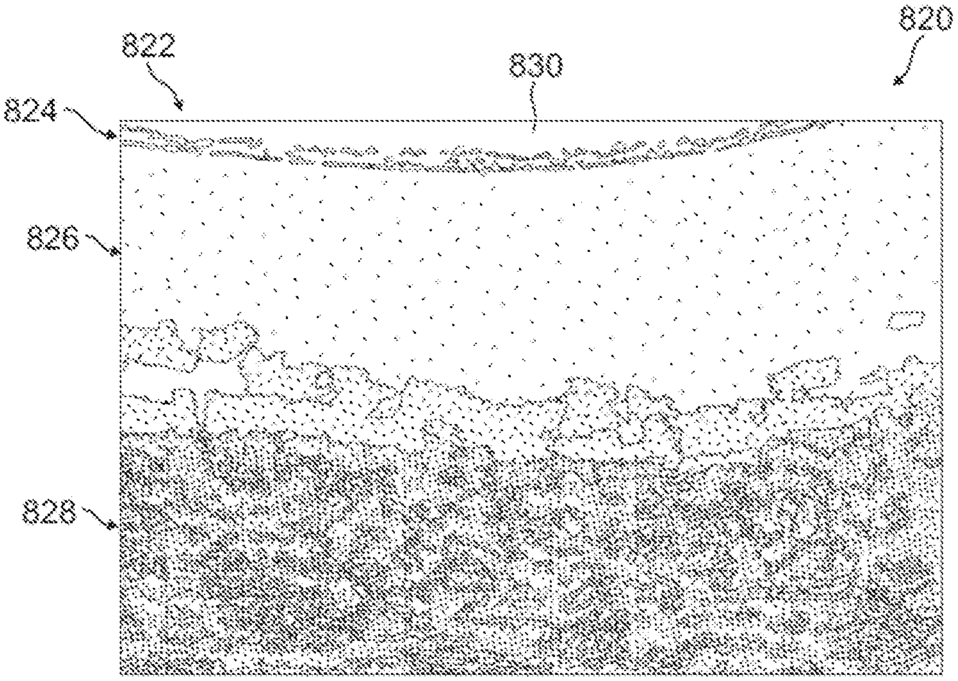
FIG. 8D is a high magnification photomicrograph of a cross-sectional view of an artery after cold therapy, in accordance with some examples of the present disclosure.

FIG. 8C is a high magnification photomicrograph of a cross-sectional view of an artery prior to cold therapy. Wall 822 defines a lumen 830, and includes a tunica intima 824, a tunica media 826, and a tunica adventitia 828. Prior to cold therapy, tunica media 826 includes both smooth muscle cells (e.g., oval structures) and structural proteins (e.g., wavy structures). FIG. 8D is a high magnification photomicrograph of a cross-sectional view of an artery after cold therapy, in accordance with some examples of the present disclosure. As seen in FIG. 8D, tunica media 826 does not include smooth muscle cells, but does include structural proteins.

The techniques described in this disclosure, including those attributed to therapy generator 30, programmer 34, cold therapy source 37, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor," "processing circuitry," "controller," or "control circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The above detailed descriptions of examples of the technology are not intended to be exhaustive or to limit the technology to the precise form disclosed above. Although specific examples of the technology are described above for illustrative purposes, various equivalent modifications are possible within the scope of the technology, as those skilled in the relevant art will recognize. For example, while steps are presented in a given order, alternative examples may perform steps in a different order. The various examples described herein may also be combined to provide further examples. All references cited herein are incorporated by reference as if fully set forth herein.

From the foregoing, it will be appreciated that specific examples of the present disclosure have been described herein for purposes of illustration, but that various modifications may be made without deviating from the present disclosure. For example, while particular features of the intravascular medical device were described as being part of a single device, in other examples, these features can be included on one or more separate devices that can be positioned adjacent to and/or used in tandem with the intravascular medical device to perform similar functions to those described herein.

Certain aspects of the present disclosure described in the context of particular examples may be combined or eliminated in other examples. Further, while advantages associated with certain examples have been described in the context of those examples, other examples may also exhibit such advantages, and not all examples need necessarily exhibit such advantages to fall within the scope of the present disclosure. Accordingly, the present disclosure and associated technology can encompass other examples not expressly shown or described herein.

Moreover, unless the word “or” is expressly limited to mean only a single item exclusive from the other items in reference to a list of two or more items, then the use of “or” in such a list is to be interpreted as including (a) any single item in the list, (b) all of the items in the list, or (c) any combination of the items in the list. Additionally, the terms “about” or “approximately,” when preceding a value, should be interpreted to mean plus or minus 10% of the value, unless otherwise indicated. Additionally, the term “comprising” is used throughout to mean including at least the recited feature(s) such that any greater number of the same feature and/or additional types of other features are not precluded.

The scope of the present disclosure includes the following non-limiting examples.

Example 1: A system includes an intravascular medical device includes a cold therapy assembly that includes one or more surfaces configured to remove heat from a wall of a vessel; and an elongated member coupled to the cold therapy assembly; and a therapeutic medical device communicatively coupled to the cold therapy assembly and configured to control the cold therapy assembly to ablate smooth muscle cells of the wall of the vessel without substantially denaturing one or more structural proteins of the wall of the vessel.

Example 2: The system of example 1, wherein the one or more structural proteins comprise elastin and collagen.

Example 3: The system of any of examples 1 and 2, wherein, to ablate the smooth muscle cells without substantially denaturing the one or more structural proteins, the therapeutic medical device is configured to control the cold therapy assembly to maintain a temperature of the smooth muscle cells within a target temperature range.

Example 4: The system of example 3, wherein the target temperature range is defined by an upper temperature threshold value associated with death of the smooth muscle cells and above a lower temperature threshold value associated with denaturing of the one or more structural proteins.

Example 5: The system of example 4, wherein the upper temperature threshold value is less than about 0° C.

Example 6: The system of any of examples 4 and 5, wherein the lower temperature threshold value is greater than about −70° C.

Example 7: The system of any of examples 1 through 6, wherein the one or more surfaces are configured to contact the wall of the vessel and remove the heat from the wall of the vessel.

Example 8: The system of any of examples 1 through 7, wherein the one or more surfaces are configured to contact a medium in the vessel and remove heat from the medium in the vessel to remove the heat from the wall of the vessel.

Example 9: The system of any of examples 1 through 8, wherein the cold therapy assembly comprises a balloon comprising a cavity configured to contain a thermal medium, the balloon defining the one or more surfaces, and wherein the one or more surfaces are configured to transfer the heat from the wall of the vessel to the thermal medium.

Example 10: The system of example 9, wherein the thermal medium comprises a cooling fluid, and wherein the therapeutic medical device is configured to control a cooling load of the cooling fluid.

Example 11: The system of example 10, wherein, to control the cooling load of the cooling fluid, the therapeutic medical device is configured to control at least one of a flow rate of the cooling fluid or a temperature of the cooling fluid.

Example 12: The system of any of examples 9 through 11, wherein the thermal medium comprises a phase change fluid, and wherein the therapeutic medical device is configured to control a cooling load of the phase change fluid.

Example 13: The system of example 12, wherein, to control the cooling load of the phase change fluid, the therapeutic medical device is configured to control a flow rate of the phase change fluid and a pressure of the phase change fluid.

Example 14: The system of any of examples 12 and 13, wherein the phase change fluid has a boiling point below about 0° C.

Example 15: The system of any of examples 9 through 14, wherein the thermal medium comprises a product of an endothermic chemical process, and wherein the therapeutic medical device is configured to control a cooling load of the endothermic chemical process.

Example 16: The system of example 15, wherein, to control the cooling load of the endothermic chemical process, the therapeutic medical device is configured to control a flow rate of at least one reactant of the endothermic chemical process to the cavity.

Example 17: The system of any of examples 9 through 16, wherein the balloon comprises one or more metallic elements configured to transfer heat from the wall of the vessel to the thermal medium.

Example 18: The system of any of examples 1 through 17, wherein the cold therapy assembly comprises a plurality of therapeutic elements that include the one or more surfaces.

Example 19: The system of example 18, wherein the plurality of therapeutic elements comprises a plurality of thermoelectric elements configured to change temperature in response to an applied voltage.

Example 20: The system of example 19, wherein the therapeutic medical device is configured to control the applied voltage to the plurality of thermoelectric elements.

Example 21: The system of any of examples 19 and 20, wherein the plurality of thermoelectric elements comprise a plurality of Peltier devices.

Example 22: The system of any of examples 19 through 21, wherein the cold therapy assembly comprises one or more channels configured to transport a coolant to remove heat from the plurality of thermoelectric elements.

Example 23: The system of any of examples 1 through 22, wherein the cold therapy assembly comprises an expansion device, and wherein the expansion device is configured to radially extend the one or more surfaces to contact the wall of the vessel.

Example 24: The system of example 23, wherein the expansion device comprises a balloon configured to transform from a delivery configuration to an inflated deployed configuration.

Example 25: The system of any of examples 23 and 24, wherein the expansion device is configured to transform from an elongated delivery configuration to a helical or a spiral deployed configuration.

Example 26: The system of any of examples 23 through 25, wherein the expansion device comprises a net expansion configured to transform from a collapsed delivery configuration to an expanded delivery configuration.

Example 27: The system of any of examples 23 through 26, wherein the expansion device is configured to expand the vessel beyond an initial diameter of the vessel.

Example 28: A method includes positioning one or more surfaces of a cold therapy assembly in thermal communication with a wall of a vessel, wherein the wall of the vessel includes smooth muscle cells and one or more structural proteins; and removing heat from the wall of the vessel to ablate the smooth muscle cells without substantially denaturing the one or more structural proteins.

Example 29: The method of example 28, wherein the one or more structural proteins comprise elastin and collagen.

Example 30: The method of any of examples 28 and 29, wherein removing heat from the wall of the vessel comprises removing heat from the wall of the vessel to maintain a temperature of the smooth muscle cells within a target temperature range for a treatment time within a target treatment time range.

Example 31: The method of example 30, wherein the target temperature range is defined by an upper temperature threshold value associated with death of the smooth muscle cells and above a lower temperature threshold value associated with denaturing of the one or more structural proteins.

Example 32: The method of example 31, wherein the upper temperature threshold value is less than about 0° C.

Example 33: The method of any of examples 31 and 32, wherein the lower temperature threshold value is greater than about −70° C.

Example 34: The method of any of examples 28 through 33, wherein the one or more surfaces contact the wall of the vessel and remove the heat from the wall of the vessel.

Example 35: The method of any of examples 28 through 34, wherein the one or more surfaces contact a medium in the vessel and remove heat from the medium in the vessel to remove the heat from the wall of the vessel.

Example 36: The method of any of examples 28 through 35, wherein the cold therapy assembly comprises a balloon comprising a cavity configured to contain a thermal medium, wherein removing the heat from the wall of the vessel comprises transmitting the heat from the wall of the vessel to the thermal medium through the one or more surfaces.

Example 37: The method of example 36, wherein the thermal medium comprises a cooling fluid, and wherein removing the heat from the wall of the vessel comprises controlling, by control circuitry, a cooling load of the cooling fluid.

Example 38: The method of example 37, wherein controlling the cooling load of the cooling fluid comprises controlling, by the control circuitry, at least one of a flow rate of the cooling fluid or a temperature of the cooling fluid.

Example 39: The method of any of examples 36 through 38, wherein the thermal medium comprises a phase change fluid, and wherein removing the heat from the wall of the vessel comprises controlling, by control circuitry, a cooling load of the phase change fluid.

Example 40: The method of example 39, wherein controlling the cooling load of the phase change fluid comprises controlling, by the control circuitry, a flow rate of the phase change fluid and a pressure of the phase change fluid.

Example 41: The method of any of examples 39 and 40, wherein the phase change fluid has a boiling point less than about 0° C.

Example 42: The method of any of examples 36 through 41, wherein the thermal medium comprises a product of an endothermic chemical process, and wherein removing the heat from the wall of the vessel comprises controlling, by the control circuitry, a cooling load of the endothermic chemical process.

Example 43: The method of example 42, wherein controlling the cooling load of the endothermic chemical process comprises controlling, by the control circuitry, a flow rate of at least one reactant of the endothermic chemical process to the cavity.

Example 44: The method of any of examples 36 through 43, wherein the balloon comprises one or more metallic elements configured to transfer heat from the wall of the vessel to the thermal medium.

Example 45: The method of any of examples 28 through 44, wherein the cold therapy assembly comprises a plurality of therapeutic elements that include the one or more surfaces.

Example 46: The method of example 45, wherein the plurality of therapeutic elements comprises a plurality of thermoelectric elements configured to change temperature in response to an applied voltage.

Example 47: The method of example 46, further comprising controlling the applied voltage to the plurality of thermoelectric elements.

Example 48: The method of any of examples 46 and 47, wherein the plurality of thermoelectric elements comprise a plurality of Peltier devices.

Example 49: The method of any of examples 46 through 48, wherein the cold therapy assembly comprises one or more channels configured to transport a coolant to remove heat from the plurality of thermoelectric elements.

Example 50: The method of any of examples 28 through 49, wherein the cold therapy assembly comprises an expansion device, and wherein contacting the wall of the vessel with the one or more surfaces comprises operating the expansion device to radially extend the one or more surfaces to contact the wall of the vessel.

Example 51: The method of example 50, wherein the expansion device comprises a balloon configured to transform from a deflated delivery configuration to an inflated deployed configuration.

Example 52: The method of any of examples 50 and 51, wherein the expansion device is configured to transform from an elongated delivery configuration to a helical or a spiral deployed configuration.

Example 53: The method of any of examples 50 through 52, wherein the expansion device comprises a net expansion device configured to transform from a collapsed delivery configuration to an expanded delivery configuration.

Example 54: The method of any of examples 50 through 53, further comprising expanding the vessel beyond an initial diameter of the vessel prior to ablating the smooth muscle cells.

Example 55: The method of any of examples 28 through 54, wherein the vessel is a constricted vessel.

Example 56: The method of any of examples 28 through 55, wherein ablating the smooth muscle cells without substantially denaturing the one or more structural proteins reduces a systemic blood pressure of a patient.

Various examples of the disclosure have been described. Any combination of the described systems, operations, or functions is contemplated. These and other examples are within the scope of the following claims.

What is claimed is:

1. A system comprising:

an intravascular medical device comprising:

a cold therapy assembly that includes one or more surfaces configured to remove heat from a wall of a vessel; and an elongated member coupled to the cold therapy assembly; and a therapeutic medical device communicatively coupled to the cold therapy assembly and configured to control the cold therapy assembly to ablate smooth muscle cells of the wall of the vessel without substantially denaturing one or more structural proteins of the wall of the vessel, wherein the therapeutic medical device is programmed to execute a therapy program that restricts a cooling load applied by the cold therapy assembly to maintain a temperature of the smooth muscle cells within a target temperature range for a treatment time within a target treatment time range such that nerves adjacent to the wall of the vessel are not substantially ablated.

2. The system of claim 1, wherein the one or more structural proteins comprise elastin and collagen.

3. The system of claim 1, wherein the target temperature range is defined by an upper temperature threshold value associated with death of the smooth muscle cells and above a lower temperature threshold value associated with denaturing of the one or more structural proteins.

4. The system of claim 3, wherein the upper temperature threshold value is less than about 0 degrees Celsius (° C.), and wherein the lower temperature threshold value is greater than about −70° C.

5. The system of claim 1, wherein the one or more surfaces are configured to contact the wall of the vessel and remove the heat from the wall of the vessel.

6. The system of claim 1, wherein the one or more surfaces are configured to contact a medium in the vessel and remove heat from the medium in the vessel to remove the heat from the wall of the vessel.

7. The system of claim 1, wherein the cold therapy assembly comprises a balloon comprising a cavity configured to contain a thermal medium, the balloon defining the one or more surfaces, and wherein the one or more surfaces are configured to transfer the heat from the wall of the vessel to the thermal medium.

8. The system of claim 7, wherein the thermal medium comprises at least one of a cooling fluid, a phase change fluid, or a product of an endothermic chemical process, and wherein the therapeutic medical device is configured to control a cooling load of the cooling fluid, the phase change fluid, or the endothermic chemical process.

9. The system of claim 8, wherein the thermal medium comprises the product of the endothermic chemical process, and wherein the therapeutic medical device is configured to control a cooling load of the endothermic chemical process.

10. The system of claim 1, wherein the cold therapy assembly comprises a plurality of therapeutic elements that include the one or more surfaces.

11. The system of claim 10, wherein the plurality of therapeutic elements comprises a plurality of thermoelectric elements configured to change temperature in response to an applied voltage.

12. The system of claim 1, wherein the cold therapy assembly comprises an expansion device, and wherein the expansion device is configured to radially extend the one or more surfaces to contact the wall of the vessel.

13. The system of claim 12, wherein the expansion device comprises a balloon configured to transform from a delivery configuration to an inflated deployed configuration.

14. The system of claim 12, wherein the expansion device is configured to transform from an elongated delivery configuration to a helical or a spiral deployed configuration.

15. The system of claim 12, wherein the expansion device comprises a net expansion configured to transform from a collapsed delivery configuration to an expanded delivery configuration.

16. The system of claim 12, wherein the expansion device is configured to expand the vessel beyond an initial diameter of the vessel.

17. The system of claim 1, wherein the therapy program restricts the cooling load applied by the cold therapy assembly such that the nerves adjacent to the wall of the vessel are not cooled to less than about 0 degrees Celsius, and such that less than about 10 percent of the nerves adjacent to the wall of the vessel are ablated.

18. A method comprising:

positioning one or more surfaces of a cold therapy assembly in thermal communication with a wall of a vessel, wherein the wall of the vessel includes smooth muscle cells and one or more structural proteins; and removing heat from the wall of the vessel to ablate the smooth muscle cells without substantially denaturing the one or more structural proteins, wherein removing the heat from the wall of the vessel includes executing a therapy program that restricts a cooling load applied by the cold therapy assembly to maintain a temperature of the smooth muscle cells within a target temperature range for a treatment time within a target treatment time range such that nerves adjacent to the wall of the vessel are not substantially ablated.

19. The method of claim 18, wherein the one or more structural proteins comprise elastin and collagen.

20. The method of claim 18, wherein the target temperature range is defined by an upper temperature threshold value associated with death of the smooth muscle cells and above a lower temperature threshold value associated with denaturing of the one or more structural proteins.

21. The method of claim 20, wherein the upper temperature threshold value is less than about 0 degrees Celsius (° C.), and wherein the lower temperature threshold value is greater than about −70° C.

22. The method of claim 18, further comprising expanding the vessel beyond an initial diameter of the vessel prior to ablating the smooth muscle cells.

23. The method of claim 18, wherein the vessel is a constricted vessel.

24. The method of claim 18, wherein ablating the smooth muscle cells without substantially denaturing the one or more structural proteins reduces a systemic blood pressure of a patient.

* * * * *